(12) United States Patent  
Cool et al.

(10) Patent No.: US 9,359,452 B2
(45) Date of Patent: Jun. 7, 2016

(54) ISOLATION AND CHARACTERISATION OF HEPARAN SULPHATES AND THEIR USE IN PHARMACEUTICAL COMPOSITIONS, METHODS OF TREATMENT AND STEM CELL CULTURE MEDIA SUITABLE FOR CONDITIONS ASSOCIATED WITH BONE REPAIR

(75) Inventors: Simon Cool, Singapore (SG); Victor Nurcombe, Singapore (SG); Murali Sadasivam, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 30 days.

(21) Appl. No.: 13/510,906

(22) PCT Filed: Nov. 19, 2010

(86) PCT No.: PCT/SG2010/000439
§ 371 (c)(1),
(2), (4) Date: May 18, 2012

(87) PCT Pub. No.: WO2011/062561
PCT Pub. Date: May 26, 2011

(65) Prior Publication Data
US 2012/0230964 A1 Sep. 13, 2012

Related U.S. Application Data

(60) Provisional application No. 61/263,283, filed on Nov. 20, 2009.

(51) Int. Cl.
A61K 31/727 (2006.01)
A61K 35/32 (2015.01)
A61P 19/00 (2006.01)
C08B 37/00 (2006.01)
A61L 27/20 (2006.01)
A61L 27/38 (2006.01)
C12N 5/0775 (2010.01)

(52) U.S. Cl.
CPC ........... *C08B 37/0075* (2013.01); *A61K 31/727* (2013.01); *A61L 27/20* (2013.01); *A61L 27/3821* (2013.01); *A61L 27/3834* (2013.01); *A61L 27/3847* (2013.01); *C12N 5/0663* (2013.01); *A61L 2430/02* (2013.01); *C12N 2500/34* (2013.01); *C12N 2502/14* (2013.01)

(58) Field of Classification Search
None
See application file for complete search history.

(56) References Cited

U.S. PATENT DOCUMENTS

2009/0137038 A1 5/2009 Nurcombe et al.
2009/0148420 A1 6/2009 Cool et al.

FOREIGN PATENT DOCUMENTS

| WO | WO96/23003 | 8/1996 |
|---|---|---|
| WO | WO00/78356 | 12/2000 |
| WO | WO2005/107772 | 11/2005 |
| WO | WO2006/085209 | 2/2006 |
| WO | WO2006/076627 | 7/2006 |
| WO | WO2010/011185 | 1/2010 |
| WO | WO2010/029278 | 3/2010 |
| WO | WO2010/030241 | 3/2010 |
| WO | WO2010/030244 | 3/2010 |

OTHER PUBLICATIONS

Luong-Van, Emma; et al; "The in vivo assessment of a novel scaffold containing heparan sulfate for tissue engineering with human mesenchymal stem cells" Journal of Molecular Histology, 38, 459-468, 2007.*
Lyon, Malcolm; et al; "Liver Heparan Sulfate Structure: A Novel Molecular Design" The Journal of Biological Chemistry, 269, 11208-11215, 1994.*
Jackson, Rebecca A; et al; "Coordinated fibroblast growth factor and heparan sulfate regulation of osteogenesis" Gene, 379, 79-91, 2006.*
Brickman et al. "Structural Modification of Fibroblast Growth Factor-binding Heparan Sulfate at a Determinative Stage of Neural Development" *J. Biol. Chem.* 273(8):4350-4359 (1998).
International Search Report and Written Opinion for PCT/SG2010/000439 dated Feb. 21, 2011.
Ledin et al., "Heparan Sulfate Structure in Mice with Genetically Modified Heparan Sulfate Production" *J. Biol. Chem.* 279(41):42732-42741 (2004).
Ledin et al., "Enzymatically Active N-Deacetylase/N-Sulfrotranferase-2 Is Present in Liver but Does Not Contribute to Heparan Sulfate N-Sulfation" *J. Biol. Chem.*, 281(47):35727-35734 (2006).
Lyon et al., "Liver Heparan Sulfate Structure," *J. Biol. Chem.*, 269(15):11208-11215 (1994).
Murali et al., "Gender Specific Mouse Liver Heparan Sulfate Modulate human Mesenchymal Stem Cell Proliferation and Differentiation: Structure and Functional Relationship".
Uygun et al., "Immobilized Glycosaminoglycans Influence Proliferation and Differentiation of Mesenchymal Stem Cells" *Tissue Engineering Part A* (2009).
Warda et al., "Isolation and characterization of heparin sulfate from various murine tissues" *Glycoonj J.* 23:555-563 (2006).
Bramono et al., Bone Marrow-Derived Heparan Sulfate Potentiate the Osteogenic Activity of Bone Morphogenetic Protein-2 (BMP-2), Bone, 50(4): 954-964 (2012).
Brickman et al., Structural Modification of Fibroblast Growth Factor-binding Heparan Sulfate at a Determinative Stage of Neural Development, The Journal of Biological Chemistry, 273(8): 4350-4359 (1998).
Murali et al., Affinity-Selected Heparan Sulfate for Bone Repair, Biomaterials, 34: 5594-5605 (2013).
Allen, B.L. and Rapraeger, A.C., Spatial and temporal expression of heparan sulfate in mouse development regulates FGF and FGF receptor assembly, The Journal of Cell Biology, 163(3): 637-648 (2003).

(Continued)

*Primary Examiner* — Renee Claytor
*Assistant Examiner* — David Berke-Schlessel
(74) *Attorney, Agent, or Firm* — Choate, Hall & Stewart LLP; Charles E. Lyon; Kristen C. Buteau

(57) ABSTRACT

Heparan sulphates isolated from male and female murine liver, their characterisation and use in pharmaceutical compositions, methods of treatment and in stem cell culture media suitable for conditions associated with bone repair.

20 Claims, 18 Drawing Sheets

(56) References Cited

OTHER PUBLICATIONS

Boutin, E.L. et al., Epithelial-Mesenchymal Interactions in Uterus and Vagina Alter the Expression of the Cell Surface Proteoglycan, Syndecan, Developmental Biology, 148: 63-74 (1991).

Feyzi, E. et al., Age-dependent Modulation of Heparan Sulfate Structure and Function, The Journal of Biological Chemistry, 272(22): 13395-13398 (1998).

Guimond, S. et al., Dynamic biosynthesis of heparan sulphate sequences in developing mouse brain: a potential regulatory mechanism during development. Biochemical Society Transactions, 29(2): 177-181 (2001).

Jenniskens, G.J. et al., Spatiotemporal Distribution of Heparan Sulfate Epitopes During Myogenesis and Synaptogenesis: A Study in Developing Mouse Intercostal Muscle, Developmental Dynamics 225:70-79 (2002).

Nurcombe, V. et al., Developmental regulation of Neural response to FGF-1 and FGF-2 by Heparan Sulfate Proteoglycan., Science, 260 (1993).

Sanderson, R.D. et al., B lymphocytes express and lose syndecan at specific stages of differentiation, Cell Regulation, 1:27-35 (1989).

Sanderson, R.D. et al., Syndecan-1, a Cell-Surface Proteoglycan, Changes in Size and Abundance when Keratinocytes Stratify, The Journal of Investigative Dermatology, 99(4): 390-396 (1992).

* cited by examiner

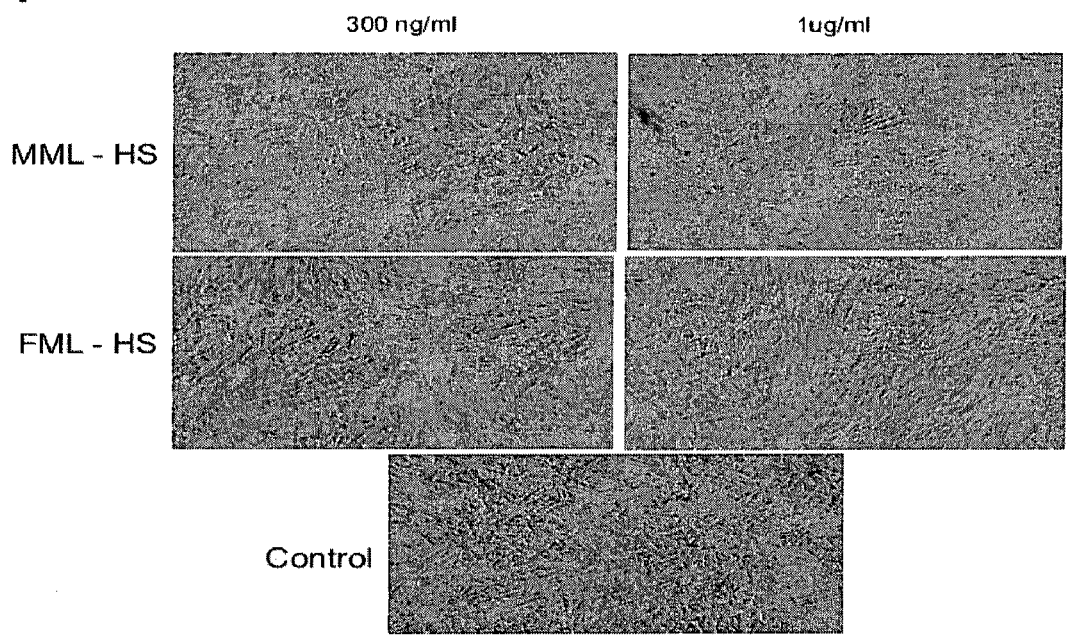
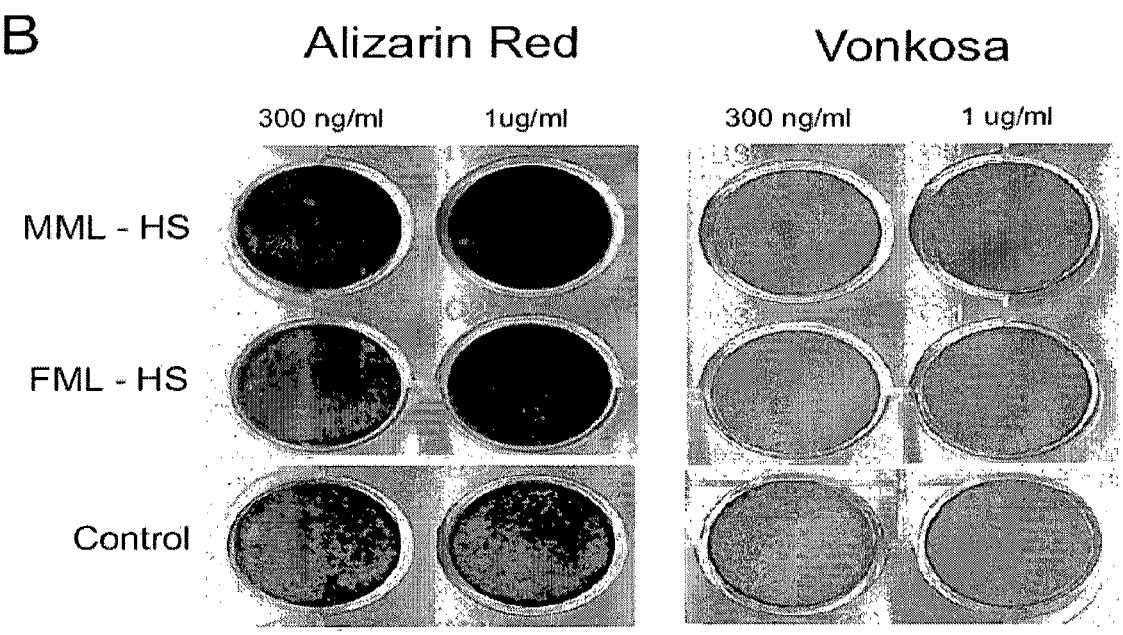
Figure 6

Table 1

| Genes | Oligo/probe | Sequences (5' to 3') |
|---|---|---|
| 18S rRNA | 18S_F<br>18S_R<br>18S_P | TTCGAGGCCCTGTAATTGGA<br>GCAGCAACTTTAATATACGCTATTGG<br>AGTCCACTTTAAATCCTT |
| Alkaline phosphatise | AP_F<br>AP_R<br>AP_P | ATGCCCTGGAGCTTCAGAAG<br>TGGTGGAGCTGACCCTTGAG<br>ACG T+GG +CT+A A+GA +AT+G T+CA +TC |
| Bone sialoprotein 2 | BSPII_F<br>BSPII_R<br>BSPII_P | AGAGGAAGCAATCACCAAAATGA<br>TTGAGAAAGCACAGGCCATTC<br>ct g+Ct +T+Ta a+Tt +Ttg +Ct+C agc |
| Osteopontin | OP_F<br>OP_R<br>OP_P | ACATCACCTCACACATGGAAAGC<br>GCTGACTCGTTTCATAACTGTCCT<br>ctt c+Tg +At+T ggg +Ac+A gc+C gt |
| RUNX2 | RX_F<br>RX_R<br>RX_P | AGGCATGTCCCTCGGTATGTC<br>GAAGGGTCCACTCTGGCTTTG<br>aca c+Ct a+Cc tg+C ca+C ca+C cc |

Figure 9

Table 2

| No | Disaccharide Standards | % Composition | |
|---|---|---|---|
| | | Male Liver HS | Female Liver HS |
| 1 | ΔHexUA-GlcN | 28±2 | 12±3 |
| 2 | ΔHexUA-GlcNAc | 14±1 | 2±1 |
| 3 | ΔHexUA-GlcN(6S) | 17±1 | 10±2 |
| 4 | ΔHexUA(2S)-GlcN | 12±1 | 8±1 |
| 5 | ΔHexUA-GlcNSO3 | 10±1 | 60±2 |
| 6 | ΔHexUA-GlcNAc(6S) | 0.5±1 | n.d |
| 7 | ΔHexUA(2S)-GlcNAc | 1.5±1 | 0.5±0.5 |
| 8 | ΔHexUA(2S)-GlcN(6S) | n.d | 0.5±0.5 |
| 9 | ΔHexUA-GlcNSO3(6S) | n.d | n.d |
| 10 | ΔHexUA(2S)-GlcNSO3 | n.d | n.d |
| 11 | ΔHexUA(2S)-GlcNAc(6S) | n.d | n.d |
| 12 | ΔHexUA(2S)-GlcNSO3(6S) | 8±2 | 2±1 |
| 13 | Unknown | 9±2 | 5±1 |

Figure 10

ISOLATION AND CHARACTERISATION OF HEPARAN SULPHATES AND THEIR USE IN PHARMACEUTICAL COMPOSITIONS, METHODS OF TREATMENT AND STEM CELL CULTURE MEDIA SUITABLE FOR CONDITIONS ASSOCIATED WITH BONE REPAIR

PRIORITY CLAIM

This application is a national phase application under 35 USC §371 of PCT International Application No. PCT/SG2010/000439 (published PCT Application No. WO/2011/062561 A1), filed Nov. 19, 2010, which claims priority from U.S. Provisional Application No. 61/263,283 filed Nov. 20, 2009, the contents of each of which arc hereby incorporated by reference in their entirety for all purposes.

SEQUENCE LISTING

In accordance with 37 CFR 1.52(e)(5), a Sequence Listing in the form of a text file (entitled "Sequence Listing.txt," created on May 18, 2012, and 4 kilobytes in size) is incorporated herein by reference in its entirety.

FIELD OF THE INVENTION

The present invention relates to heparan sulphates isolated from male murine liver and female murine liver.

BACKGROUND TO THE INVENTION

Heparan sulfate proteoglycan (HSPGs) structure consists of a core protein to which one or more linear glycosaminoglycans (GAGs) chains are attached at specific serine-glycine residues. Heparan sulfates (HSs) have complex sulfated domain structures, which are initially synthesized as non-sulfated polysaccharides of D-glucuronic acid-N-acetyl-D-glucosamine (GlcA-GlcNAc) repeats (1-4). Concurrent with polymerization of the HS chain, a series of enzymatic modifications occur that generate the diverse sulphated domains at intervals along a growing chain. The non-template-driven diversity of HS structure thus is able to give rise to a wide range of biological functions.

Several studies have demonstrated that the binding of growth factors to HS and thus giving rise to mitogenic activity happens only when specific structural features are present within the HS chain (5). Such features include sulfation at specific positions within a disaccharide; 6-O sulphated, N-sulfated glucosamine and 2-O sulfated iduronic acid residues are particularly important, and minimum binding sequences are generally at least 5-6 disaccharides in length (6-8). The precise structures of HS that are involved in these interactions have remained elusive. Knowledge of the variations in composition and organization of HS from different cells and tissues is becoming increasingly essential as attempts are made to elucidate the relationship between HS structure and function. Each tissue type bears a unique complement of HS structures that may also vary at different stages of tissue development (4,9). It is clear that particular heparan sulphate structures are expressed in different tissue types and at different time during development, and these different structures are selectively recognized by heparan sulphate binding proteins; thus for example, differing complements of HS appear to change the way that heparin/HS-dependent growth factors such as the FGFs exert their mitogenic and differentiative effects within developing tissues (10).

Our group has previously shown that HS plays a role in osteogenic differentiation of a preosteoblast MC3T3 cells (11), furthermore, exogenous application of HS to cultures of rat bone marrow stem cells (rMSCs) stimulate their proliferation leading to increased expression of osteogenic markers and enhanced bone nodule formation (12). In recent years human mesenchymal stem cells (hMSC) have been demonstrated to be an alternative cell source for tissue engineering applications. These cells are easy to isolate and can be highly expanded by various tissue culture techniques. These cells are differentiated into a variety of mesenchymal tissues (13), such as osteoblasts (14,15), adipocytes (16), myocytes, astrocytes and neurons (17,18).

Recently gender specific HS were purified from murine tissues and showed that the disaccharide composition of HS chains from the same tissue with different genders are structurally different (19). However comparative structural and functional analysis of the gender specific HS from murine tissue have not been undertaken to date.

SUMMARY OF THE INVENTION

The inventors have now isolated specific (and separate) heparan sulphates from male and female mouse liver, and have called them male mouse liver heparan sulphate (MML HS) and female mouse liver heparan sulphate (FML HS).

MML HS and FML HS have separately and individually been demonstrated to exhibit strong growth effects on human mesenchymal stem cells (hMSCs), without the addition of exogenous growth factors. MML HS has been shown to increase proliferation of hMSCs in culture in a dose dependent manner.

MML HS and FML HS have also been shown to, separately and individually, exhibit strong facilitation of differentiation of human mesenchymal stem cells towards the osteogenic lineage, promoting osteogenic differentiation and matrix mineralisation of human mesenchymal stem cells in a dose dependent manner and without the addition of exogenous growth factors.

MML HS and FML HS have been shown to be structurally different in terms of both gross and fine structure. This is reflected by differences in the effect of MML HS and FML HS on proliferation of hMSC during culture in growth and osetogenic media.

In growth medium, MML HS dose dependently increases the cell number of hMSC, with the highest cell number being obtained with the highest concentration of HS tested (12.5 µg/ml).

However, FML HS at lower concentration (152 ng/ml) was found to lead to a greater increase in hMSC cell number compared with the highest concentration of FML HS tested (12.5 µg/ml).

In osteogenic medium, MML HS at lower concentration (312 ng/ml) was found to lead to the highest increase in cell number, whilst FML HS at the highest concentration tested (12.5 µg/ml) yielded the largest increase in cell number.

The inventors' results clearly show that MML HS and FML HS each (individually) increase hMSC mineralization in a dose dependent manner, although MML HS at lower concentrations was found to lead to an equivalent increase in mineralization as that achieved with higher concentrations of FML HS.

Accordingly, the inventors have shown that exogenous application of murine liver heparan sulfate can increase the growth of mesenchymal stem cells from a bone marrow aspirate above those taken from conventional culture techniques. Thus, murine liver derived heparan sulphates offer a novel means for decreasing the expansion time necessary for obtaining large numbers of mutipotent adult stem cells for therapeutic use without the addition of exogenous growth factors that compromise stem cell fate.

In one aspect of the present invention heparan sulphate MML HS is provided. MML HS may be provided in isolated or substantially purified form. This may comprise providing a composition in which the heparan sulphate component is at least 80% MML HS, more preferably one of at least 85%, 90%, 95%, 96%, 97%, 98%, 99% or 100%.

MML HS preferably has N-sulfation of between about 14% and about 22%.

MML HS has:
(i) total sulfation of between about 60% and about 70%; and/or
(ii) total O-sulfation of between about 44% and about 52%; and/or
(iii) N-sulfation of between about 14% and about 22%; and/or
(iv) 6-O-sulfation of between about 22% and about 30%; and/or
(v) 2-O-sulfation of between about 18% and about 26%.

In some preferred embodiments MML HS has:
(i) total sulfation of about 65% or about 66%; and/or
(ii) total O-sulfation of about 47%, about 48% or about 49%; and/or
(iii) N-sulfation of about 17%, about 18% or about 19%; and/or
(iv) 6-O-sulfation of about 25%, about 26% or about 27%; and/or
(v) 2-O-sulfation of about 21%, about 22% or about 23%.

MML HS has an N-unsubstituted disaccharide content of between about 53% and about 61%. In some preferred embodiments MML HS has an N-unsubstituted disaccharide content of about 56%, about 57% or about 58%.

MML HS has a disaccharide composition that is within ±10% of the values shown for each disaccharide in the Male Liver HS column in Table 2. In some preferred embodiments MML HS has a disaccharide composition within ±5% of the values shown for each disaccharide in the Male Liver HS column in Table 2.

MML HS is obtainable by a method comprising conducting size exclusion chromatography on a male mouse liver heparan sulphate preparation to identify heparan sulphate fractions of different molecular weight followed by selection of the major high molecular weight fraction.

MML HS is provided for use in a method of medical treatment, for example use in the treatment of bone fracture.

Compositions comprising MML HS are provided. In some embodiments the composition is a pharmaceutical composition or medicament comprising MML HS, optionally in combination with a pharmaceutically acceptable diluent, adjuvant or carrier. Pharmaceutical compositions or medicaments according to the present invention may comprise MML HS together with a therapeutically effective amount of mesenchymal stem cells. The pharmaceutical compositions or medicaments may be provided for use in a method of medical treatment, for example use in the treatment of bone fracture. The use of MML HS in the manufacture of a medicament for the treatment of bone fracture is also provided.

A method of treating a bone fracture in a patient is also provided, the method comprising administration of a therapeutically effective amount of MML HS to the patient. The method may comprise administering MML HS to the tissue surrounding the fracture, which may include injection of MML HS to the tissue surrounding the fracture. The method may further comprise administering mesenchymal stem cells to the patient, which may also be administered to the tissue surrounding The fracture, e.g. at the same site to which the MML HS is administered.

Another method of treating a bone fracture in a patient is also provided, the method comprising surgically implanting a biocompatible implant or prosthesis, which implant or prosthesis comprises a biomaterial and MML HS, into tissue of the patient at or surrounding the site of fracture.

A biocompatible implant or prosthesis comprising a biomaterial and MML HS is also provided. A method of forming a biocompatible implant or prosthesis is also provided, the method comprising the step of coating or impregnating a biomaterial with MML HS.

Culture media comprising MML HS is also provided as well as the use of MML HS in cell culture in vitro. A method of culturing cells in vitro comprising the step of adding MML HS to cells in in vitro culture, preferably such that the MML HS comes into contact with the cells, is also provided.

The use of MML HS in the culture and/or growth of stem cells, bone cells, bone precursor cells or bone tissue in vitro is provided. Accordingly, a method for the culture and/or growth of stem cells, bone cells, bone precursor cells or bone tissue in vitro is provided, the method comprising administering MML HS to the cells/tissue in culture such that the MML HS is allowed to contact the cells/tissue. The method may involve increasing the rate of proliferation of the cells or tissue as compared with culture of the cells or tissue in the absence of MML HS. Administration of MML HS will normally involve addition of MML. HS to the culture, i.e. introducing an amount of MML HS to the culture that is effective to increase the growth and/or proliferation of the cells/tissue.

A method of promoting osteogenesis is also provided, the method comprising administering MML HS to bone precursor cells or bone stem cells. The method may involve promoting or facilitating the differentiation of cells into bone precursor cells or bone cells or bone tissue. The process of osteogenesis may be monitored by following the expression of osteogenic marker proteins such as Alkaline Phosphatase, Bone Sialoprotein 2, Osteopontin and/or Runx2. Additionally or alternatively, the process of osteogenesis may be followed by monitoring the mineralisation of the cultured cells/tissue, e.g. by staining of cells/tissue with Alizarin red S or von Kossa stains. In some embodiments the bone precursor cells or bone stem cells are contacted with MML HS in vitro. In other embodiments the bone precursor cells or bone stem cells are contacted with MML HS in vivo, wherein the method may form part of a method of treatment of a patient, e.g. treatment of bone fracture in a patient. Administration of MML HS to cells in order to promote osetogenesis will normally involve addition of MML HS to the cells, i.e. introducing an amount of MML HS to the cells that is effective to promote osteogenesis of the cells. In some embodiments the bone precursor or bone stem cells are mesenchymal stem cells.

A method for the repair, replacement or regeneration of bone tissue in a human or animal patient in need of such treatment is provided, the method comprising:
(i) culturing mesenchymal stem cells in vitro in contact with MML HS for a period of time sufficient for said cells to form bone tissue or bone precursor cells;
(ii) collecting said bone tissue or bone precursor cells;
(iii) implanting said bone tissue or bone precursor cells into the body of the patient at a site of injury or disease to repair, replace or regenerate bone tissue in the patient.

Bone tissue or bone precursor cells obtained by in vitro culture of mesenchymal stem cells in the presence of MML HS is also provided.

Additionally, a method of culturing mesenchymal stem cells is provided, the method comprising culturing mesenchymal stem cells in contact with MML HS.

Products containing therapeutically effective amounts of: (i) MML HS; and (ii) mesenchymal stem cells, for simultaneous, separate or sequential use in a method of medical treatment are also provided.

In another aspect of the present invention heparan sulphate FML HS is provided. FML HS may be provided in isolated or substantially purified form. This may comprise providing a composition in which the heparan sulphate component is at least 80% FML HS, more preferably one of at least 85%, 90%, 95%, 96%, 97%, 98%, 99% or 100%.

FML HS preferably has N-sulfation of between about 57% and about 66%.

FML HS has:
 (i) total sulfation of between about 80% and about 90%; and/or
 (ii) total O-sulfation of between about 19% and about 27%; and/or
 (iii) N-sulfation,of between about 57% and about 66%; and/or
 (iv) 6-O-sulfation of between about 8% and about 16%; and/or
 (v) 2-O-sulfation of between about 7% and about 15%.

In some preferred embodiments FML HS has:
 (i) total sulfation of about 84%, about 85% or about 86%; and/or
 (ii) total O-sulfation of about 22%, about 23% or about 24%; and/or
 (iii) N-sulfation of about 60%, about 61%, about 62% or about 63%; and/or
 (iv) 6-O-sulfation of about 11%, about 12% or about 13%; and/or
 (v) 2-O-sulfation of about 10%, about 11% or about 12%.

FML HS has an N-unsubstituted disaccharide content of between about 26% and about 34%. In some preferred embodiments FML HS has an N-unsubstituted disaccharide content of about 29%, about 30% or about 31%

FML HS has a disaccharide composition that is within ±10% of the values shown for each disaccharide in the Female Liver HS column in Table 2. In some preferred embodiments FML HS has a disaccharide composition within ±5% of the values shown for each disaccharide in the Female Liver HS column in Table 2.

FML HS is obtainable by a method comprising conducting size exclusion chromatography on a female mouse liver heparan sulphate preparation to identify heparan sulphate fractions of different molecular weight followed by selection of the major low molecular weight fraction.

FML HS is provided for use in a method of medical treatment, for example use in the treatment of bone fracture.

Compositions comprising FML HS are provided. In some embodiments the composition is a pharmaceutical composition or medicament comprising FML HS, optionally in combination with a pharmaceutically acceptable diluent, adjuvant or carrier. Pharmaceutical compositions or medicaments according to the present invention may comprise FML HS together with a therapeutically effective amount of mesenchymal stem cells. The pharmaceutical compositions or medicaments may be provided for use in a method of medical treatment, for example use in the treatment of bone fracture. The use of FML HS in the manufacture of a medicament for the treatment of bone fracture is also provided.

A method of treating a bone fracture in a patient is also provided, the method comprising administration of a therapeutically effective amount of FML HS to the patient. The method may comprise administering FML HS to the tissue surrounding the fracture, which may include injection of FML HS to the tissue surrounding the fracture. The method may further comprise administering mesenchymal stem cells to the patient, which may also be administered to the tissue surrounding the fracture, e.g. at the same site to which the FML HS is administered.

Another method of treating a bone fracture in a patient is also provided, the method comprising surgically implanting a biocompatible implant or prosthesis, which implant or prosthesis comprises a biomaterial and FML HS, into tissue of the patient at or surrounding the site of fracture.

A biocompatible implant or prosthesis comprising a biomaterial and FML HS is also provided. A method of forming a biocompatible implant or prosthesis is also provided, the method comprising the step of coating or impregnating a biomaterial with FML HS.

Culture media comprising FML HS is also provided as well as the use of FML HS in cell culture in vitro. A method of culturing cells in vitro comprising the step of adding FML HS to cells in in vitro culture, preferably such that the FML HS comes into contact with the cells, is also provided.

The use of FML HS in the culture and/or growth of stem cells, bone cells, bone precursor cells or bone tissue in vitro is provided. Accordingly, a method for the culture and/or growth of stem cells, bone cells, bone precursor cells or bone tissue in vitro is provided, the method comprising administering FML HS to the cells/tissue in culture such that the FML HS is allowed to contact the cells/tissue. The method may involve increasing the rate of proliferation of the cells or tissue as compared with culture of the cells or tissue in the absence of FML HS. Administration of FML HS will normally involve addition of FML HS to the culture, i.e. introducing an amount of FML HS to the culture that is effective to increase the growth and/or proliferation of the cells/tissue.

A method of promoting osteogenesis is also provided, the method comprising administering FML HS to bone precursor cells or bone stem cells. The method may involve promoting or facilitating the differentiation of cells into bone precursor cells or bone cells or bone tissue. The process of osteogenesis may be monitored by following the expression of osteogenic marker proteins such as Alkaline Phosphatase, Bone Sialoprotein 2, Osteopontin and/or Runx2. Additionally or alternatively, the process of osteogenesis may be followed by monitoring the mineralisation of the cultured tissue, e.g. by staining of cells/tissue with Alizarin red S or von Kossa stains. In some embodiments the bone precursor cells or bone stem cells are contacted with FML HS in vitro. In other embodiments the bone precursor cells or bone stem cells are contacted with FML HS in vivo, and the method may thereby form part of a method of treatment of a patient, e.g. treatment of bone fracture in a patient. Administration of FML HS to cells in order to promote osetogenesis will normally involve addition of FML HS to the cells, i.e. introducing an amount of FML HS to the cells that is effective to promote osteogenesis of the cells. In some embodiments the bone precursor or bone stem cells are mesenchymal stem cells.

A method for the repair, replacement or regeneration of bone tissue in a human or animal patient in need of such treatment is provided, the method comprising:
 (i) culturing mesenchymal stem cells in vitro in contact with FML HS for a period of time sufficient for said cells to form bone tissue or bone precursor cells;
 (ii) collecting said bone tissue or bone precursor cells;

(iii) implanting said bone tissue or bone precursor cells into the body of the patient at a site of injury or disease to repair, replace or regenerate bone tissue in the patient.

Bone tissue or bone precursor cells obtained by in vitro culture of mesenchymal stem cells in the presence of FML HS is also provided.

Additionally, a method of culturing mesenchymal stem cells is provided, the method comprising culturing mesenchymal stem cells in contact with FML HS.

Products containing therapeutically effective amounts of: (i) FML HS; and (ii) mesenchymal stem cells, for simultaneous, separate or sequential use in a method of medical treatment are also provided.

DESCRIPTION OF PREFERRED EMBODIMENTS

The present invention relates to two novel heparan sulphates, respectively obtained from male and female mouse liver. They have been called male mouse liver heparan sulphate (MML HS) and female mouse liver heparan sulphate (FML HS).

MML HS and FML HS may each be provided in isolated or substantially purified form. They may also be provided as mixtures of compounds (e.g. mixtures of glycosaminoglycans or heparan sulphates) enriched with MML HS or FML HS. Methods of using MML HS or FML HS, and of using such mixtures, are described including their use in in vitro culture of cells and their use in medical methods such as the treatment of bone fracture.

As described herein, MML HS and FML HS have been found to increase proliferation of hMSC in in vitro culture.

Also as described herein, MML HS and FML HS have been found to increase osteogenic differentiation of hMSC and bone mineralisation in a dose dependent manner.

Heparan Sulphate is a naturally occurring constituent of mammalian cells that acts by catalyzing molecular encounters between growth factors and their endogenous receptors. As such it provides increased specificity and sensitivity over traditional techniques used to expand stem cell numbers that rely on dosing cultures with large concentrations of growth factors. Since the cells make sufficient growth factors themselves, simply by adding the correct HS variant we are able to sustain stem cell expansion without the need for exogenous growth factor supplements. That is, there is no requirement for exogenous application of growth factors during adult stem cell expansion when cells are cultured in MML HS or FML HS. Accordingly, in some preferred embodiments methods of cell culture according to the present invention can be carried out without exogenous addition of growth factors in amounts normally effective (or required) to maintain the viability, or increase the growth and/or proliferation and/or differentiation, of the cultured cells.

Accordingly, MML HS and FML HS are each provided (separately or in combination) for use (in vitro or in vivo) in the stimulation of stem cell proliferation and/or for use in bone formation, regeneration and repair.

The murine liver as a source of heparan sulphate represents a scalable tissue source of heparan sulphate since the liver is a large organ that is easily extracted and the heparan sulphate purified.

Heparan sulphates isolated by enrichment from murine liver may be pure, i.e. contain substantially only one type of heparan sulphate, or may continue to be a mixture of different types of heparan sulphates, the mixture having a higher proportion of a particular heparan sulphate (i.e. MML HS and/or FML HS).

As used herein, the terms 'enriching', 'enrichment', 'enriched', etc. describes a process (or state) whereby the relative composition of a mixture is (or has been) altered in such a way that the fraction of that mixture given by one or more of those entities is increased, while the fraction of that mixture given by one or more different entities is decreased.

MML HS or FML HS preferably exhibit a functional effect when contacted with cells. The functional effect may be to promote (stimulate) the proliferation of cells of a certain type or the differentiation of one cell type into another, or the expression of one or more protein markers.

For example, each of MML HS and FML HS preferably promote cell proliferation, i.e. an increase in cell number, or promote differentiation of stem cells into specialised cell types (e.g. mesenchymal stem cells into bone or bone precursor cells/tissue), promote or inhibit the expression of protein markers indicative of the multipotency or differentiation state of the cells (e.g. markers such as alkaline phosphatase, RUNX2, osteopontin, BSP2).

MML HS and FML HS may be useful in a range of applications, in vitro and/or in vivo. Each may be provided for use in stimulation or inhibition of stem cell growth and/or proliferation and/or differentiation either in cell or tissue culture in vitro, or in cells or tissue in vivo.

MML HS and FML HS may be provided as a composition or formulation for such purposes. For example, culture media may be provided comprising MML HS, or FML HS.

Cells or tissues obtained from in vitro cell or tissue culture in the presence of MML HS or FML HS may be collected and implanted into a human or animal patient in need of treatment. A method of implantation of cells and/or tissues may therefore be provided, the method comprising the steps of:
(a) culturing cells and/or tissues in vitro in contact with MML HS or FML HS;
(b) collecting the cells and/or tissues;
(c) implanting the cells and/or tissues into a human or animal subject in need of treatment.

The cells may be cultured in part (a) in contact with MML HS or FML HS for a period of time sufficient to allow growth, proliferation or differentiation of the cells or tissues. For example, the period of time may be chosen from: at least 5 days, at least 10 days, at least 20 days, at least 30 days or at least 40 days.

In other embodiments MML HS or FML HS may be formulated for use in a method of medical treatment, including the prevention or treatment of injury or disease. A pharmaceutical composition or medicament may be provided comprising MML HS or FML HS and a pharmaceutically acceptable diluent, carrier or adjuvant. Such pharmaceutical compositions or medicaments may be provided for the prevention or treatment of injury or disease. The use of MML HS or FML HS in the manufacture of a medicament for the prevention or treatment of injury or disease is also provided. In some embodiments the pharmaceutical compositions and medicaments may further comprise stem cells, e.g. mesenchymal stem cells.

Treatment of injury or disease may comprise the repair, regeneration or replacement of cells or tissue, particularly bone tissue. For the repair or regeneration of tissue, the pharmaceutical composition or medicament comprising MML HS or FML HS may be administered directly to the site of injury or disease in order to stimulate the growth, proliferation and/or differentiation of new tissue to effect a repair of the injury or to cure or alleviate (e.g. provide relief to the symptoms of) the disease condition. The repair or regeneration of the tissue may be improved by combining stem cells in the pharmaceutical composition or medicament.

For the replacement of tissue, MML HS or FML HS may be contacted with cells and/or tissue during in vitro culture of the cells and/or tissue in order to generate cells and/or tissue for implantation at the site of injury or disease in the patient. Implantation of cells or tissue can be used to effect a repair of the injured or diseased tissue in the patient by replacement of the injured or diseased tissue. This may involve excision of injured/diseased tissue and implantation of new tissue prepared by culture of cells and/or tissue in contact with MML HS or FML HS.

Pharmaceutical compositions and medicaments according to the present invention may therefore comprise one of:
    (a) MML HS or FML HS;
    (b) MML HS or FML HS in combination with stem cells;
    (c) Tissues or cells obtained from culture of cells or tissues in contact with MML HS or FML HS.

MML HS or FML HS may be used in the repair or regeneration of bodily tissue, especially bone regeneration, and in the expansion and self-renewal of stem cells. Accordingly, MML HS or FML HS may be used to prevent or treat a wide range of diseases and injuries, including osteoarthritis, broken bones of any kind (e.g. spinal disc fusion treatments, long bone breaks, cranial defects), critical or non-union bone defect regeneration.

The use of MML HS or FML HS in the repair, regeneration or replacement of tissue may involve use in wound healing, e.g. acceleration of wound healing, healing of scar or bone tissue and tissue grafting.

In another aspect, the present invention provides a biological scaffold comprising MML HS or FML HS. In some embodiments, the biological scaffolds of the present invention may be used in orthopaedic, vascular, prosthetic, skin and corneal applications. The biological scaffolds provided by the present invention include extended-release drug delivery devices, tissue valves, tissue valve leaflets, drug-eluting stents, vascular grafts, wound healing or skin grafts and orthopaedic prostheses.

In another aspect, the present invention provides pharmaceutically acceptable formulations comprising a mixture of compounds comprising one or more glycosaminoglycans, said mixture being enriched with respect to MML HS or FML HS. The glycosaminoglycan content of the formulation may have at least 50% MML HS or FML HS, more preferably one of at least 60%, 70%, 75%, 80%, 85%, 90%, 95%, 96%, 97%, 98%, 99% or 100%.

In another aspect of the present invention a kit is provided for use in the repair, or regeneration of bone tissue, said kit comprising a predetermined amount of MML HS or FML HS.

The compounds of the enriched mixtures of the present invention can be administered to a subject as a pharmaceutically acceptable salt thereof. For example, base salts of the compounds of the enriched mixtures of the present invention include, but are not limited to, those formed with pharmaceutically acceptable cations, such as sodium, potassium, lithium, calcium, magnesium, ammonium and alkylammonium. The present invention includes within its scope cationic salts, for example the sodium or potassium salts.

Medicaments and pharmaceutical compositions according to aspects of the present invention may be formulated for administration by a number of routes, including but not limited to, injection at the site of disease or injury. The medicaments and compositions may be formulated in fluid or solid form. Fluid formulations may be formulated for administration by injection to a selected region of the human or animal body.

The subject to be treated may be any animal or human. The subject may be a non-human mammal. The subject may be a non-human mammal (e.g. rabbit, guinea pig, rat, mouse or other rodent (including from any animal in the order Rodentia), cat, dog, pig, sheep, goat, cattle (including cows, e.g. dairy bows, or any animal in the order Bos), horse (including any animal in the order Equidae), donkey, and non-human primate). The non-human mammal may be a domestic pet, or animal kept for commercial purposes, e.g. a race horse, or farming livestock such as pigs, sheep or cattle. The subject may be male or female. The subject may be a patient.

Methods according to the present invention may be performed in vitro or in vivo, as indicated. The term "in vitro" is intended to encompass procedures with cells in culture whereas the term "in vivo" is intended to encompass procedures with intact multi-cellular organisms.

MML HS

One aspect of the present invention relates to Male Mouse Liver Heparan Sulphate (MML HS).

MML HS can be identified and characterised by reference to its structure arid function, and is obtainable from male mouse liver from a range of ages, but especially from 3 months to 6 months of age.

MML HS may be identified or obtained by enriching for a high molecular weight mouse liver heparan sulphate fraction. As set out herein, this enrichment may be achieved by performing size exclusion chromatography.

As described below, MML HS is obtainable by conducting size exclusion chromatography on a male mouse liver heparan sulphate preparation to identify heparan sulphate fractions of varying molecular weight followed by selection of the major high molecular weight fraction.

Size exclusion chromatography (e.g. DEAE anion-exchange chromatography followed by separation on a Superdex 75 column (GE Healthcare)) has been used to obtain MML HS. Initial size exclusion chromatography of mouse liver heparan sulphates showed that male mouse liver heparan sulphates contain a major high molecular weight peak and a smaller small molecular weight peak (FIG. 1A).

The high molecular weight heparan sulphate was treated to release associated (poly)peptide(s) and fractionated (e.g. on a Superdex 200 column (GE Healthcare)) to determine the size of the intact heparan sulphate chain.

These techniques were used to show that MML HS elutes from a Superdex 200 column with a Kav of about 0.31 (e.g. between about 0.29 and 0.33, or between about 0.30 and 0.32) and has an intact chain size of about 100 kDa (see FIGS. 1A and C).

Accordingly, MML HS according to the present invention preferably has an intact chain size of between about 90 and about 110 kDa, more preferably one of between about 95 and about 105 kDa, between about 96 and about 104 kDa, between about 97 and about 103 kDa, between about 98 and about 102 kDa, between about 99 and about 101 kDa, or about 110 kDa.

Calibration of the size exclusion column used to elute MML HS with heparin oligosaccharide size standards (e.g. Dp2 to Dp26) was used to show that MML HS is composed of approximately 30-40 or 40-50 disaccharide repeats.

Accordingly, MML HS according to the present invention may have one of between about 25 and about 55 disaccharide repeats, between about 27 and about 53 disaccharide repeats, between about 30 and about 50 disaccharide repeats, between about 30 and about 40 disaccharide repeats, between about 32 and about 38 disaccharide repeats, between about 40 and about 50 disaccharide repeats, or between about 42 and about 48 disaccharide repeats.

Size exclusion chromatography of MML HS following digestion with one of Heparinase I, II or III was used to generate profiles (of absorbance at 232 nm) of MML HS following digestion with one of Heparinase I, II or III (FIGS. 2A, C and E respectively).

Heparin lyases may also be used to exhaustively digest an heparan sulphate to its constituent disaccharides. Following such digestion strong anion-exchange high performance liquid chromatography (SAX HPLC) was used to generate a profile (of absorbance at 232 nm) of the disaccharide composition of MML HS (FIG. 3A).

This analysis was used to characterise the structure of MML HS in terms of disaccharide percentage composition (see Table 2).

The disaccharide composition of MML HS is shown in Table 2 (FIG. 10). MML HS according to the present invention includes heparan sulphate that has a disaccharide composition within ±10% (more preferably ±one of 9%, 8%, 7%, 6%, 5%, 4%, 3%, 2%, or 1%) of the values shown for each disaccharide in Table 2.

Accordingly, MML HS according to the present invention may include HS having a heparin lyase digestion disaccharide composition wherein each disaccharide corresponding to those shown in Table 2 (FIG. 10) is present and the percentage composition of each disaccharide is no more than 10%, 5%, 4%, 2% or 1%, greater or less than the percentage composition shown in Table 2.

MML HS was further characterised by analysis of the percentage composition of sulphated and N-unsubstituted disaccharides, as analysed by SAX-HPLC. As summarised in FIG. 4A, MML HS was found to have:
- a total sulfation of about 65-66%,
- ~48% total O-sulfation
- ~18% N-sulfation,
- about 26% 6-O-sulfation,
- about 22% 2-O-sulfation,
- about 57% N-unsubstituted disaccharides.

Accordingly, MML HS according to the present invention may include HS having one or more of:
- a total sulfation of one of between about 60% and about 70%, between about 62% and about 68%, between about 64% and about 67%, or about 65% or about 66%;
- total O-sulfation of one of between about 44% and about 52%, between about 46% and about 50%, or one of about 47%, about 48% or about 49%;
- N-sulfation of one of between about 14% and about 22%, between about 16% and about 20%, or one of about 17%, about 18% or about 19%;
- 6-O-sulfation of one of between about 22% and about 30%, between about 24% and about 28%, or one of about 25%, about 26% or about 27%;
- 2-O-sulfation of one of between about 18% and about 26%, between about 20% and about 24%, or one of about 21%, about 22% or about 23%;
- an N-unsubstituted disaccharide content of one of between about 53% and about 61%, between about 55% and about 59%, or one of about 56%, about 57% or about 58%.

The sensitivity of a heparan sulphate to heparin lyase digestion is at least partially a consequence of its structure and therefore sensitivity to heparinase I, II or III can be used to assist in structural characterisation of an heparan sulphate.

MML HS was found not to be particularly sensitive to cleavage by heparinases I or II, but heparinase III cleaved about 80% of the MML HS chains mainly into di- and tetrasaccharides.

The structural data generated for MML HS has been used to generate a predicted structure of MML HS, shown in FIG. 8. In FIG. 8, when units are repeated, they are designated such as "4 units" (the unit being repeated 4 times). The Superdex 200 sizing column profile showed that intact MML HS chains are composed of 30-40 or 40-50 disaccharides repeats. MML HS chains appear to consist of a substantial proportion of alternating acetylated glucosamine sequence (GlcA-GlcNAc) in the reducing end (NA domain) and N-unsubstituted glucosamine are the major proportion of mixed sequences in the middle of the HS chain, which contains $\Delta HexA\text{-}GlcNH_3^+$, $\Delta HexA\text{-}GlcNH_3^+(6S)$, $\Delta HexA(2S)\text{-}GlcNH_3^+$, $\Delta HexA(2S)\text{-}GlcNAc(6S)$ and a minor portion of $\Delta HexA\text{-}GlcNSO_3$ (NA/NS domain). There are also a relatively minor proportion of about 4-5 trisulfated disaccharides ($\Delta HexA(2S)\text{-}GlcNS(6S)$) within the sequence on the S-domain in the non-reducing end.

The inventors also investigated the functional properties of MML HS, in particular its effect on human mesenchymal stem cells (hMSCs).

MML HS was found to increase both the proliferation and differentiation of hMSC in in vitro culture.

In particular, MML HS exhibits a dose dependent increase in hMSC number. De-N-sulfated MML HS was found not to increase hMSC when compared to exposure of hMSC to 10% serum and therefore N-sulfation of MML HS is considered important as regards its effect on proliferation of hMSC.

MML HS was also found to affect osteogenic differentiation of hMSC and matrix mineralisation, indicating that it can be used in facilitating the development of bone tissue from hMSCs.

In particular, MML HS was found to increase hMSC mineralisation in a dose dependent manner, with extensive mineralisation being present at 21 days after induction of differentiation (FIG. 6).

The facilitating effect of MML HS on osteogenic differentiation of hMSC is supported by the upregulation of expression of osteogenic marker genes alkaline phosphatase (ALP), bone sialoprotein 2 (BSP2), osteopontin (OPN) and Runx2. ALP expression was upregulated within 7 days of exposure to MML HS (FIG. 7), which is consistent with ALP being an essential transcription factor for osteoblast differentiation that is expressed early in osteogenic differentiation. Expression of BSP2, OPN and Runx2 were all upregulated at day 21 following exposure to MML HS (FIG. 7).

FML HS

One aspect of the present invention relates to Female Mouse Liver Heparan Sulphate (FML HS).

FML HS can be identified and characterised by reference to its structure and function, and is obtainable from male mouse liver from a range of ages, but especially from 3 months to 6 months of age.

As described below, FML HS is obtainable by conducting size exclusion chromatography on a female mouse liver heparan sulphate preparation to identify heparan sulphate fractions of varying molecular weight followed by selection of the major high molecular weight fraction.

FML HS may be identified or obtained by enriching for a low molecular weight mouse liver heparan sulphate fraction. As set out herein, this enrichment may be achieved by performing size exclusion chromatography.

Size exclusion chromatography (e.g. DEAE anion-exchange chromatography followed by separation on a Superdex 75 column (GE Healthcare)) has been used to obtain FML HS. Initial size exclusion chromatography of mouse liver heparan sulphates showed that female mouse liver heparan sulphates contain a major low molecular weight peak and a smaller high molecular weight peak (FIG. 1B).

The low molecular weight heparan sulphate was treated to release associated (poly)peptide(s) and fractionated (e.g. on a Superdex 200 column (GE Healthcare)) to determine the size of the intact heparan sulphate chain.

These techniques were used to show that FML HS elutes from a Superdex 200 column with a Kav of about 0.54 (e.g. between about 0.53 and 0.56, or between about 0.53 and 0.55) and has an intact chain size of about 22 kDa (see FIGS. 1B and D).

Accordingly, FML HS according to the present invention preferably has an intact chain size of between about 12 and about 32 kDa, more preferably one of between about 17 and about 27 kDa, between about 18 and about 26 kDa, between about 19 and about 25 kDa, between about 20 and about 24 kDa, between about 21 and about 23 kDa, or about 22 kDa.

Calibration of the size exclusion column used to elute FML HS with heparin oligosaccharide size standards (e.g. Dp2 to Dp26) was used to show that FML HS is composed of approximately 6-8 disaccharide repeats.

Accordingly, FML HS according to the present invention may have one of between about 4 and about 18 disaccharide repeats, between about 4 and about 12 disaccharide repeats, between about 6 and about 10 disaccharide repeats, or one of about 6, about 7, about 8, about 9, or about 10 disaccharide repeats.

Size exclusion chromatography of FML HS following digestion with one of Heparinase I, II or III was used to generate profiles (of absorbance at 232 nm) of FML HS following digestion with one of Heparinase I, II or III (FIGS. 2B, D and F respectively).

Heparin lyases may also be used to exhaustively digest an heparan sulphate to its constituent disaccharides. Following such digestion strong anion-exchange high performance liquid chromatography (SAX HPLC) was used to generate a profile (of absorbance at 232 nm) of the disaccharide composition of FML HS (FIG. 3B).

This analysis was used to characterise the structure of FML HS in terms of disaccharide percentage composition (see Table 2).

The disaccharide composition of FML HS is shown in Table 2 (FIG. 10). FML HS according to the present invention includes heparan sulphate that has a disaccharide composition within ±10% (more preferably ± one of 9%, 8%, 7%, 6%, 5%, 4%, 3%, 2%, or 1%) of the values shown for each disaccharide in Table 2.

Accordingly, FML HS according to the present invention may include HS having a heparin lyase digestion disaccharide composition wherein each disaccharide corresponding to those shown in Table 2 (FIG. 10) is present and the percentage composition of each disaccharide is no more than 10%, 5%, 4%, 2%. or 1%, greater or less than the percentage composition shown in Table 2.

FML HS was further characterised by analysis of the percentage composition of sulphated and N-unsubstituted disaccharides, as analysed by SAX-HPLC. As summarised in FIG. 4A, FML HS was found to have:
  a total sulfation of about 85%,
  about 23% total O-sulfation,
  about 61-62% N-sulfation,
  about 12% 6-O-sulfation,
  about 11% 2-O-sulfation,
  about 30% N-unsubstituted disaccharides.

Accordingly, FML HS according to the present invention may include HS having one or more of:
  a total sulfation of one of between about 80% and about 90%, between about 82% and about 88%, between about 84% and about 87%, or about 84%, about 85% or about 86%;
  total O-sulfation of one of between about 19% and about 27%, between about 21% and about 25%, or one of about 22%, about 23% or about 24%;
  N-sulfation of one of between about 57% and about 66%, between about 59% and about 64%, or one of about 60%, about 61%, about 62% or about 63%;
  6-O-sulfation of one of between about 8% and about 16%, between about 10% and about 14%, or one of about 11%, about 12% or about 13%;
  2-O-sulfation of one of between about 7% and about 15%, between about 9% and about 13%, or one of about 10%, about 11% or about 12%;
  an N-unsubstituted disaccharide content of one of between about 26% and about 34%, between about 28% and about 32%, or one of about 29%, about 30% or about 31%.

The sensitivity of a heparan sulphate to heparin lyase digestion is at least partially a consequence of its structure and therefore sensitivity to heparinase I, II or III can be used to assist in structural characterisation of an heparan sulphate.

FML HS was found to have high sensitivity to each of Heparinases I, II and III. In particular, exposure to Heparinase I led to ~65% of linkages being cleaved to yield dp2-dp6 as the major product with an ~35% yield of longer oligosaccharides, and exposure to Heparinase III led to complete degradation into di- and tetrasaccharides, which was considered to be a unique feature of FML HS.

The structural data generated for FML HS has been used to generate a predicted structure of FML HS, shown in FIG. 8. The Superdex 200 sizing column profile showed that the intact FML HS chains were composed of 6-8 disaccharides repeats. The FML HS chains appear to consist of a major proportion of N-sulfated glucosamine (ΔHexA-GlcNSO$_3$) and also a substantial proportion of N-unsubstituted glucosamine in the middle of the HS chain, which contains ΔHexA-GlcNH$_3^+$, ΔHexA-GlcNH$_3^+$(6S), ΔHexA(2S)-GlcNH$_3^+$ (NAINS domain). There is also a minor proportion of ΔHexA-GlcNAc present on the reducing end (N-acetyl domain) and also a minor proportion of ΔHexA(2S)-GlcNS (6S) present on the non-reducing end (N-sulfated domain).

The inventors also investigated the functional properties of FML HS, in particular its effect on human mesenchymal stem cells (hMSCs).

FML HS was found to increase both the proliferation and differentiation of hMSC in in vitro culture.

De-N-sulfated FML HS was found not to increase hMSC when compared to exposure of hMSC to 10% serum and therefore N-sulfation of FML HS is considered important as regards its effect on proliferation of hMSC.

FML HS was also found to affect osteogenic differentiation of hMSC and matrix mineralisation, indicating that it can be used in facilitating the development of bone tissue from hMSCs.

In particular, FML HS was found to increase hMSC mineralisation in a dose dependent manner, with extensive mineralisation being present at 21 days after induction of differentiation (FIG. 6).

The facilitating effect of FML HS on osteogenic differentiation of hMSC is supported by the upregulation of expression of osteogenic marker genes alkaline phosphatase (ALP), bone sialoprotein 2 (BSP2), osteopontin (OPN) and Runx2. ALP expression was upregulated within 7 days of exposure to FML HS (FIG. 7), which is consistent with ALP being an essential transcription factor for osteoblast differentiation that is expressed early in osteogenic differentiation. Expression of BSP2, OPN and Runx2 were all upregulated at day 21 following exposure to FML HS (FIG. 7).

Heparan Sulphate (HS)

Heparan sulfate proteoglycans (HSPGs) represent a highly diverse subgroup of proteoglycans and are composed of heparan sulfate glycosaminoglycan side chains covalently attached to a protein backbone. The core protein exists in three major forms: a secreted form known as perlecan, a form anchored in the plasma membrane known as glypican, and a transmembrane form known as syndecan. They are ubiquitous constituents of mammalian cell surfaces and most extracellular matrices. There are other proteins such as agrin, or the amyloid precursor protein, in which an HS chain may be attached to less commonly found cores.

"Heparan Sulphate" ("Heparan sulfate" or "HS") is initially synthesised in the Golgi apparatus as polysaccharides consisting of tandem repeats of D-glucuronic acid (GlcA) and N-acetyl-D-glucosamine (GlcNAc). The nascent polysaccharides may be subsequently modified in a series of steps: N-deacetylation/N-sulfation of GlcNAc, C5 epimerisation of GlcA to iduronic acid (IdoA), O-sulphation at C2 of IdoA and GlcA, O-sulphation at C6 of N-sulphoglucosamine (GlcNS) and occasional O-sulphation at C3 of GlcNS. N-deacetylation/N-sulphation, 2-O-, 6-O- and 3-O-sulphation of HS are mediated by the specific action of HS N-deacetylase/N-sulfotransferase (HSNDST), HS 2-O-sulfotransferase (HS2ST), HS 6-O-sulfotransferase (HS6ST) and HS 3-O-sulfotransferase, respectively. At each of the modification steps, only a fraction of the potential substrates are modified, resulting in considerable sequence diversity. This structural complexity of HS has made it difficult to determine its sequence and to understand the relationship between HS structure and function.

Heparan sulfate side chains consist of alternately arranged D-glucuronic acid or L-iduronic acid and D-glucosamine, linked via (1→4) glycosidic bonds. The glucosamine is often N-acetylated or N-sulfated and both the uronic acid and the glucosamine may be additionally O-sulfated. The specificity of a particular HSPG for a particular binding partner is created by the specific pattern of carboxyl, acetyl and sulfate groups attached to the glucosamine and the uronic acid. In contrast to heparin, heparan sulfate contains less N- and O-sulfate groups and more N-acetyl groups. The heparan sulfate side chains are linked to a serine residue of the core protein through a tetrasaccharide linkage (-glucuronosyl-β-(1→3)-galactosyl-β-(1→3)-galactosyl-β-(1→4)-xylosyl-β-1-O-(Serine)) region.

Both heparan sulfate chains and core protein may undergo a series of modifications that may ultimately influence their biological activity. Complexity of HS has been considered to surpass that of nucleic acids (Lindahl et al, 1998, J. Biol. Chem. 273, 24979; Sugahara and Kitagawa, 2000, Curr. Opin. Struct. Biol. 10, 518). Variation in HS species arises from the synthesis of non-random, highly sulfated sequences of sugar residues which are separated by unsulfated regions of disaccharides containing N-acetylated glucosamine. The initial conversion of N-acetylglucosamine to N-sulfoglucosamine creates a focus for other modifications, including epimerization of glucuronic acid to iduronic acid and a complex pattern of O-sulfations on glucosamine or iduronic acids. In addition, within the non-modified, low sulfated, N-acetylated sequences, the hexuronate residues remain as glucuronate, whereas in the highly sulfated N-sulfated regions, the C-5 epimer iduronate predominates. This limits the number of potential disaccharide variants possible in any given chain but not the abundance of each. Most modifications occur in the N-sulfated domains, or directly adjacent to them, so that in the mature chain there are regions of high sulfation separated by domains of low sulfation (Brickman et al. (1998), J. Biol. Chem. 273(8), 4350-4359, which is herein incorporated by reference in its entirety).

It is hypothesized that the highly variable heparan sulfate chains play key roles in the modulation of the action of a large number of extracellular ligands, including regulation and presentation of growth and adhesion factors to the cell, via a complicated combination of autocrine, juxtacrine and paracrine feedback loops, so controlling intracellular signaling and thereby the differentiation of stem cells. For example, even though heparan sulfate glycosaminoglycans may be genetically described (Alberts et al. (1989) Garland Publishing, Inc, New York & London, pp. 804 and 805), heparan sulfate glycosaminoglycan species isolated from a single source may differ in biological activity. As shown in Brickman et al, 1998, Glycobiology 8, 463, two separate pools of heparan sulfate glycosaminoglycans obtained from neuroepithelial cells could specifically activate either FGF-1 or FGF-2, depending on mitogenic status. Similarly, the capability of a heparan sulfate (HS) to interact with either FGF-1 or FGF-2 is described in WO 96/23003. According to this patent application, a respective HS capable of interacting with FGF-1 is obtainable from murine cells at embryonic day from about 11 to about 13, whereas a HS capable of interacting with FGF-2 is obtainable at embryonic day from about 8 to about 10.

As stated above HS structure is highly complex and variable between HS. Indeed, the variation in HS structure is considered to play an important part in contributing toward the different activity of each HS in promoting cell growth and directing cell differentiation. The structural complexity is considered to surpass that of nucleic acids and although HS structure may be characterised as a sequence of repeating disaccharide units having specific and unique sulfation patterns at the present time no standard sequencing technique equivalent to those available for nucleic acid sequencing is available for determining HS sequence structure. In the absence of simple methods for determining a definitive HS sequence structure HS molecules are positively identified and structurally characterised by skilled workers in the field by a number of analytical techniques. These include one or a combination of disaccharide analysis, tetrasaccharide analysis, HPLC and molecular weight determination. These analytical techniques are well known to and used by those of skill in the art.

Two techniques for production of di- and tetra-saccharides from HS include nitrous acid digestion and lyase digestion. A description of one way of performing these digestion techniques is provided below, purely by way of example, such description not limiting the scope of the present invention.

Nitrous Acid Digestion

Nitrous acid based depolymerisation of heparan sulphate leads to the eventual degradation of the carbohydrate chain into its individual disaccharide components when taken to completion.

For example, nitrous acid may be prepared by chilling 250 µl of 0.5 M $H_2SO_4$ and 0.5 M $Ba(NO_2)_2$ separately on ice for 15 min. After cooling, the $Ba(NO_2)_2$ is combined with the $H_2SO_4$ and vortexed before being centrifuged to remove the barium sulphate precipitate. 125 µl of $HNO_2$ is added to GAG samples resuspended in 20 µl of $H_2O$, and vortexed before being incubated for 15 min at 25° C. with occasional mixing. After incubation, 1 M $Na_2CO_3$ is added to the sample to bring it to pH 6. Next, 100 µl of 0.25 M $NaBH_4$ in 0.1 M NaOH is added to the sample and the mixture heated to 50° C. for 20 min. The mixture is then cooled to 25° C. and acidified glacial acetic acid added to bring the sample to pH 3. The mixture is then neutralised with 10 M NaOH and the volume decreased by freeze drying. Final samples are run on a Bio-Gel P-2 column to separate di- and tetrasaccharides to verify the degree of degradation.

Lyase Digestion

Heparinise III cleaves sugar chains at glucuronidic linkages. The series of Heparinase enzymes (I, II and III) each display relatively specific activity by depolymerising certain heparan sulphate sequences at particular sulfation recognition sites. Heparinase I cleaves HS chains with NS regions along the HS chain. This leads to disruption of the sulphated domains. Heparinase III depolymerises HS with the NA domains, resulting in the separation of the carbohydrate chain into individual sulphated domains. Heparinase II primarily cleaves in the NA/NS "shoulder" domains of HS chains, where varying sulfation patterns are found. Note: The repeating disaccharide backbone of the heparan polymer is a uronic acid connected to the amino sugar glucosamine. "NS" means the amino sugar is carrying a sulfate on the amino group enabling sulfation of other groups at C2, C6 and C3. "NA" indicates that the amino group is not sulphated and remains acetylated.

For example, for depolymerisation in the NA regions using Heparinase III both enzyme and lyophilised HS samples are prepared in a buffer containing 20 mM Tris-HCL, 0.1 mg/ml BSA and 4 mM $CaCl_2$ at pH 7.5. Purely by way of example, Heparinase III may be added at 5 mU per 1 μg of HS and incubated at 37° C. for 16 h before stopping the reaction by heating to 70° C. for 5 min.

Di- and tetrasaccharides may be eluted by column chromatography.

Stem Cells

Cells contacted with MML HS or FML HS include stem cells.

The stem cells cultured and described herein may be stem cells of any kind. They may be totipotent or multipotent (pluripotent). They may be embryonic or adult stem cells from any tissue and may be hematopoietic stem cells, neural stem cells or mesenchymal stem cells. Preferably they are adult stem cells. More preferably they are adult mesenchymal stem cells, e.g. capable of differentiation into connective tissue and/or bone cells such as chondrocytes, osteoblasts, myocytes and adipocytes. The stem cells may be obtained from any animal or human, e.g. non-human animals, e.g. rabbit, guinea pig, rat, mouse or other rodent (including cells from any animal in the order Rodentia), cat, dog, pig, sheep, goat, cattle, horse, non-human primate or other non-human vertebrate organism; and/or non-human mammalian animals; and/or human. Optionally they are non-human.

In this specification, by stem cell is meant any cell type that has the ability to divide (i.e. self-renew) and remain totipotent or multipotent (pluripotent) and give rise to specialized cells if so desired.

Stem cells cultured in the present invention may be obtained or derived from existing cultures or directly from any adult, embryonic or fetal tissue, including blood, bone marrow, skin, epithelia or umbilical cord (a tissue that is normally discarded).

The multipotency of stem cells may be determined by use of suitable assays. Such assays may comprise detecting one or more markers of pluripotency, e.g. alkaline phosphatase activity, detection of RUNX2, osterix, collagen I, II, IV, VII, X, osteopontin, Osteocalcin, Aggrecan, ALBP, CCAAT/enhancer binding protein-α (C/EBPα), adipocyte lipid binding protein (ALBP), bone sialoprotein 2, (BSPII), Collagen2a1 (Col2a) and SOX9.

Mesenchymal stem cells or human bone marrow stromal stem cells are defined as pluripotent (multipotent) progenitor cells with the ability to generate cartilage, bone, muscle, tendon, ligament and fat. These primitive progenitors exist postnatally and exhibit stem cell characteristics, namely low incidence and extensive renewal potential. These properties in combination with their developmental plasticity have generated tremendous interest in the potential use of mesenchymal stem cells to replace damaged tissues. In essence mesenchymal stem cells could be cultured to expand their numbers then transplanted to the injured site or after seeding in/on scaffolds to generate appropriate tissue constructs.

Thus, an alternative approach for skeletal, muscular, tendon and ligament repair is the selection, expansion and modulation of the appropriate progenitor cells such as osteoprogenitor cells in the case of bone in combination with a conductive or inductive scaffold to support and guide regeneration together with judicious selection of specific tissue growth factors.

Human bone marrow mesenchymal stem cells can be isolated and detected using selective markers, such as STRO-I, from a CD34+ fraction indicating their potential for marrow repopulation. These cell surface markers are only found on the cell surface of mesenchymal stem cells and are an indication of cell pluripotency.

Mesenchymal stem cells are easily obtainable from bone marrow by minimally invasive techniques and can be expanded in culture and permitted to differentiate into the desired lineage. Differentiation can be induced by the application of specific growth factors. The transforming growth factor beta (TGF-beta) superfamily member proteins such as the bone morphogenetic proteins (BMPs) are important factors of chondrogenic and osteogenic differentiation of mesenchymal stem cells.

Suitable MSCs may be obtained or derived from bone marrow mononuclear cells (BMMNCs) collected from aspirates of bone marrow (e.g. Wexler et al. Adult bone marrow is a rich source of human mesenchymal 'stem' cells but umbilical cord and mobilized adult blood are not. HAEMOPOIESIS AND LEUCOCYTES *British Journal of Haematology* 121 (2):368-374, April 2003.) or Wharton's Jelly of the umbilical cord (e.g. Ta et al. Long-term Expansion and Pluripotent Marker Array Analysis of Wharton's Jelly-Derived Mesenchymal Stem Cells. *Stem Cells Dev.* 2009 Jul. 20 (Epub)).

Mesenchymal stem cells may be obtained by differentiation of pluripotent stem cells, such as human embryonic stem cells or induced pluripotent stem cells, by application of suitable differentiating factors, as is well known in the art.

In a further aspect of the present invention, a pharmaceutical composition comprising stem cells generated by any of the methods of the present invention, or fragments or products thereof, is provided. The pharmaceutical composition useful in a method of medical treatment. Suitable pharmaceutical compositions may further comprise a pharmaceutically acceptable carrier, adjuvant or diluent.

In another aspect of the present invention, stem cells generated by any of the methods of the present invention may be used in a method of medical treatment, preferably, a method of medical treatment is provided comprising administering to an individual in need of treatment a therapeutically effective amount of said medicament or pharmaceutical composition.

Stem cells obtained through culture methods and techniques according to this invention may be used to differentiate into another cell type for use in a method of medical treatment. Thus, the differentiated cell type may be derived from, and may be considered as a product of, a stem cell obtained by the culture methods and techniques described which has subsequently been permitted to differentiate. Pharmaceutical compositions may be provided comprising such differentiated cells, optionally together with a pharmaceutically acceptable carrier, adjuvant or diluent. Such pharmaceutical compositions may be useful in a method of medical treatment.

Bone Cells, Bone Precursor Cells

In accordance with the present invention MML HS and FML HS are provided for use in the culture of cells. In some embodiments the cells may be bone precursor cells. These may be stem cells capable of differentiation into cells of the osetogenic lineage. One example of bone precursor cells are mesenchymal stem cells. Cells of the osteogenic lineage include bone cells or bone-forming cells, examples of which include osteoblasts and osteocytes.

Bone Fracture

In some aspects the present invention is concerned with the therapeutic use (human and/or veterinary) of MML HS or FML HS to treat bone fracture. MML HS and FML HS are each reported here to separately enhance osteogenic differentiation in a dose dependent manner.

Bone fracture is a medical condition. In this application "fracture" includes damage or injury to bone in which a bone is cracked, broken or chipped. A break refers to discontinuity in the bone. A fracture may be caused by physical impact, or mechanical stress or by medical conditions such as osteoporosis or osteoarthritis.

Orthopaedic classification of fractures includes closed or open and simple or multi-fragmentary fractures. In closed fractures the skin remains intact, whilst in an open fracture the bone may be exposed through the wound site, which brings a higher risk of infection. Simple fractures occur along a single line, tending to divide the bone in two. Multi-fragmentary fractures spilt the bone into multiple pieces.

Other fracture types include, compression fracture, compacted fracture, spiral fracture, complete and incomplete fractures, transverse, linear and oblique fractures and comminuted fractures.

In most subjects bone healing (fracture union) occurs naturally and is initiated following injury. Bleeding normally leads to clotting and attraction of white blood cells and fibroblasts, followed by production of collagen fibres. This is followed by bone matrix (calcium hydroxyapatite) deposition (mineralisation) transforming the collagen matrix into bone. Immature re-generated bone is typically weaker than mature bone and over time the immature bone undergoes a process of remodelling to produce mature "lamellar" bone. The complete bone healing process takes considerable time, typically many months.

Bones in which fractures occur and which may benefit from treatment using MML HS or FML HS include all bone types, particularly all mammalian bones including, but not limited to, long bones. (e.g. femur, humerus, phalanges), short bones (e.g. carpals, tarsals), flat bones (e.g. cranium, ribs, scapula, sternum, pelvic girdle), irregular bones (e.g. vertebrae), sesamoid bones (e.g. patella).

Bones in which fractures occur and which may benefit from treatment using MML HS or FML HS include skeletal bone (i.e. any bone of the skeleton), bones of the cranio-facial region, bones of the axial skeleton (e.g. vertebrae, ribs), appendicular bone (e.g. of the limbs), bone of the pelvic skeleton (e.g. pelvis).

Bones in which fractures occur and which may benefit from treatment using MML HS or FML HS also include those of the head (skull) and neck, including those of the face such as the jaw, nose and cheek. In this respect, in some preferred embodiments MML HS or FML HS may be used to assist in repair or regeneration of bone during dental or facial or cranial surgery, which may include reconstruction of bones (as distinct from teeth) of the face and/or mouth, e.g. including the jawbone.

Bone fracture also includes, pathological porosity, such as that exhibited by subjects with osteoporosis.

Although not limiting to the present invention, the primary actions of MML HS or FML HS may be on cells within, adjacent to, or caused to migrate into the wound site and may be on the bone stem cells, the preosteoblasts or the osteoblasts, or on any of the ancillary or vasculogenic cells found within or caused to migrate into the wound bed.

MML HS or FML HS and pharmaceutical compositions and medicaments comprising MML HS or FML HS are provided for use in a method of treatment of bone fracture in a mammalian subject.

Treatment may comprise wound healing in bone. The treatment may involve repair, regeneration and growth of bone.

Treatment may also include treatment of osteoporosis or osteoarthritis.

Administration of MML HS or FML HS is preferably to the tissue surrounding the fracture. This may include administration directly to bone tissue in which the fracture has occurred. Administration may be to connective tissue surrounding the bone or fracture or to vasculature (e.g. blood vessels) near to and supplying the bone. Administration may be directly to the site of injury and may be to a callus formed by initial healing of the wound.

Medicaments and pharmaceutical compositions according to the present invention may be formulated for administration by a number of routes. Most preferably MML HS or FML HS is formulated in fluid or liquid form for injection.

In some embodiments the MML HS or FML HS is formulated as a controlled release formulation, e.g. in a drug capsule for implantation at the wound site. The MML HS or FML HS may be attached to, impregnated on or soaked into a carrier material (e.g. a biomaterial) such as nanofibres or biodegradable paper or textile.

Administration of MML HS or FML HS is preferably in a "therapeutically effective amount", this being sufficient to improve healing of the bone fracture compared to a corresponding untreated fracture. The actual amount administered, and rate and time-course of administration, will depend on the nature and severity of the fracture. Prescription of treatment, e.g. decisions on dosage etc, is within the responsibility of general practitioners and other medical doctors, and will typically take account of the nature of the fracture, the condition of the individual patient, the site of delivery, the method of administration and other factors known to practitioners. Single or multiple administrations of MML HS or FML HS doses may be administered in accordance with the guidance of the prescribing medical practitioner. Purely by way of example, MML HS or FML HS may be delivered in dosages of at least 1 ng/ml, more preferably at least 5 ng/ml and optionally 10 ng/ml or more. Individual MML HS or FML HS dosages may be of the order less than 1 mg and greater than 1 µg, e.g. one of about 5 µg, about 10 µg, about 25 µg, about 30 µg, about 50 µg, about 100 µg, about 0.5 mg, or about 1 mg. Examples of the techniques and protocols mentioned above can be found in Remington's Pharmaceutical Sciences, 20th Edition, 2000, pub. Lippincott, Williams & Wilkins.

MML HS or FML HS may be used to treat bone fracture alongside other treatments, such as administration of pain relieving or anti-inflammatory medicaments, immobilisation and setting of the bone, e.g. immobilising the injured limb in a plaster cast, surgical intervention, e.g. to re-set a bone or move a bone to correct displacement, angulation or dislocation. If surgery is required MML HS or FML HS may be administered directly to (e.g. applied to) the fracture during the surgical procedure.

Biomaterials

Pharmaceutical compositions and medicaments of the invention may take the form of a biomaterial that is coated and/or impregnated with MML HS or FML HS. An implant or prosthesis may be formed from the biomaterial. Such implants or prostheses may be surgically implanted to assist in bone growth, regeneration, restructuring and/or re-modelling.

MML HS or FML HS may be applied to implants or prostheses to accelerate new bone formation at a desired location. It will be appreciated that heparan sulphates, unlike proteins, are particularly robust and have a much better ability to withstand the solvents required for the manufacture of synthetic bioscaffolds and application to implants and prostheses.

The biomaterial may be coated or impregnated with MML HS or FML HS. Impregnation may comprise forming the biomaterial by mixing MML HS or FML HS with the constitutive components of the biomaterial, e.g. during polymerisation, or absorbing MML HS or FML HS into the biomaterial. Coating may comprise absorbing the MML HS or FML HS onto the surface of the biomaterial.

The biomaterial should allow the coated or impregnated MML HS or FML HS to be released from the biomaterial when administered to or implanted in the subject. Biomaterial release kinetics may be altered by altering the structure, e.g. porosity, of the biomaterial.

In addition to coating or impregnating a biomaterial with MML HS or FML HS, one or more biologically active molecules may be impregnated or coated on the biomaterial. For example, at least one chosen from the group consisting of: BMP-2, BMP-4, OP-1, FGF-1, FGF-2, TGF-β1, TGF-β2, TGF-β3; VEGF; collagen; laminin; fibronectin; vitronectin. In addition or alternatively to the above bioactive molecules, one or more bisphosphonates may be impregnated or coated onto the biomaterial along with MML HS or FML HS. Examples of useful bisphosphonates may include at least one chosen from the group consisting of: etidronate; clodronate; alendronate; pamidronate; risedronate; zoledronate.

Biomaterials coated or impregnated with MML HS or FML HS may be useful in both medical and veterinary purposes. It will be appreciated that the present invention may improve the quality of life of a patient or potentially extend the life of an animal, for example a valuable racehorse for use in breeding.

The biomaterial provides a scaffold or matrix support. The biomaterial may be suitable for implantation in tissue, or may be suitable for administration (e.g. as microcapsules in solution).

The implant or prosthesis should be biocompatible, e.g. non-toxic and of low immunogenicity (most preferably non-immunogenic). The biomaterial may be biodegradable such that the biomaterial degrades as wound healing occurs, ultimately leaving only the regenerated bone in situ in the subject. Alternatively a non-biodegradable biomaterial may be used, e.g. to guide bone regeneration over a large discontinuity and/or to act as a structural support during bone healing, with surgical removal of the biomaterial being an optional requirement after successful wound healing.

Biomaterials may be soft and/or flexible, e.g. hydrogels, fibrin web or mesh, or collagen sponges. A "hydrogel" is a substance formed when an organic polymer, which can be natural or synthetic, is set or solidified to create a three-dimensional open-lattice structure that entraps molecules of water or other solutions to form a gel. Solidification can occur by aggregation, coagulation, hydrophobic interactions or cross-linking.

Alternatively biomaterials may be relatively rigid structures, e.g. formed from solid materials such as plastics or biologically inert metals such as titanium.

The biomaterial may have a porous matrix structure which may be provided by a cross-linked polymer. The matrix is preferably permeable to nutrients and growth factors required for bone growth.

Matrix structures may be formed by crosslinking fibres, e.g. fibrin or collagen, or of liquid films of sodium alginate, chitosan, or other polysaccharides with suitable crosslinkers, e.g. calcium salts, polyacrylic acid, heparin. Alternatively scaffolds may be formed as a gel, fabricated by collagen or alginates, crosslinked using well established methods known to those skilled in the art.

Suitable polymer materials for matrix formation include, but are not limited by, biodegradable/bioresorbable polymers which may be chosen from the group of: agarose, collagen, fibrin, chitosan, polycaprolactone, poly(DL-lactide-co-caprolactone), poly(L-lactide-co-caprolactone-co-glycolide), polyglycolide, polylactide, polyhydroxyalcanoates, co-polymers thereof, or non-biodegradable polymers which may be chosen from the group of: cellulose acetate; cellulose butyrate, alginate, polysulfone, polyurethane, polyacrylonitrile, sulfonated polysulfone, polyamide, polyacrylonitrile, polymethylmethacrylate, co-polymers thereof.

Collagen is a promising material for matrix construction owing to its biocompatibility and favourable property of supporting cell attachment and function (U.S. Pat. No. 5,019,087; Tanaka, S.; Takigawa, T.; Ichihara, S. & Nakamura, T. Mechanical properties of the bioabsorbable polyglycolic acid-collagen nerve guide tube *Polymer Engineering & Science* 2006, 46, 1461-1467). Clinically acceptable collagen sponges are one example of a matrix and are well known in the art (e.g. from Integra Life Sciences).

Fibrin scaffolds (e.g. fibrin glue) provide an alternative matrix material. Fibrin glue enjoys widespread clinical application as a wound sealant, a reservoir to deliver growth factors and as an aid in the placement and securing of biological implants (Rajesh Vasita, Dhirendra S Katti. Growth factor delivery systems for tissue engineering: a materials perspective. *Expert Reviews in Medical Devices*. 2006; 3(1): 29-47; Wong C, Inman E, Spaethe R, Helgerson S. *Thromb. Haemost*. 2003 89(3): 573-582; Pandit. A S, Wilson D J, Feldman D S. Fibrin scaffold as an effective vehicle for the delivery of acidic growth factor (FGF-1). *J. Biomaterials Applications*. 2000; 14(3); 229-242; DeBlois Cote M F. Doillon C J. Heparin-fibroblast growth factor fibrin complex: in vitro and in vivo applications to collagen based materials. *Biomaterials*. 1994; 15(9): 665-672.).

Luong-Van et al (In vitro biocompatibility and bioactivity of microencapsulated heparan sulphate *Biomaterials* 28 (2007) 2127-2136), incorporated herein by reference, describes prolonged localised delivery of HS from polycaprolactone microcapsules.

A further example of a biomaterial is a polymer that incorporates hydroxyapatite or hyaluronic acid.

One example of a biomaterial suitable for use in combination with MML HS or FML HS is the JAX™ bone void filler (Smith & Nephew). Jax granules are composed of high purity calcium sulfate and retain their shape to provide a scaffold with controlled, inter-granular porosity and granule migration stability. Jax granules dissolve safely and completely in the body.

Other suitable biomaterials include ceramic or metal (e.g. titanium), hydroxyapatite, tricalcium phosphate, demineralised bone matrix (DBM), autografts (i.e. grafts derived from the patient's tissue), or allografts (grafts derived from the tissue of an animal that is not the patient). Biomaterials may be synthetic (e.g. metal, fibrin, ceramic) or biological (e.g. carrier materials made from animal tissue, e.g. non-human mammals (e.g. cow, pig), or human).

The biomaterial can be supplemented with additional cells. For example, one can "seed" the biomaterial (or co-synthesise it) with undifferentiated bone precursor cells, e.g. stem cells such as mesenchymal stem cells, more preferably human mesenchymal stem cells.

Culture Media

Culture media comprising MML HS or FML HS may be of any kind but is preferably liquid or gel and may optionally contain other nutrients and optionally growth factors (e.g. FGF-2). MML HS or FML HS will preferably be present in non-trace amounts. For example, the concentration of MML HS or FML HS in the culture media may range between about 1.0 ng/ml culture media to about 15 µg/ml culture media. For example, the concentration of MML HS or FML HS in the culture media may be between one of about 5 ng/ml culture media and about 200 ng/ml culture media, between about 200 ng/ml culture media and about 400 ng/ml culture media, between about 400 ng/ml culture media and about 600 ng/ml culture media, between about 600 ng/ml culture media and about 800 ng/ml culture media, between about 1 µg/ml culture media and about 5 µg/ml culture media, between about 5 µg/ml culture media and about 10 µg/ml culture media, and between about 10 µg/ml culture media and about 15 µg/ml culture media.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which:

FIG. 9. Table 1—Primers for Real-Time RT-PCR.

FIG. 10. Table 2—Lyase-derived disaccharide percentage compositions of soluble, cell surface and matrix HS. The area under each peak was integrated to calculate the percentage of each disaccharides. n.d=not detected.

DETAILED DESCRIPTION OF THE INVENTION

Figure 1:
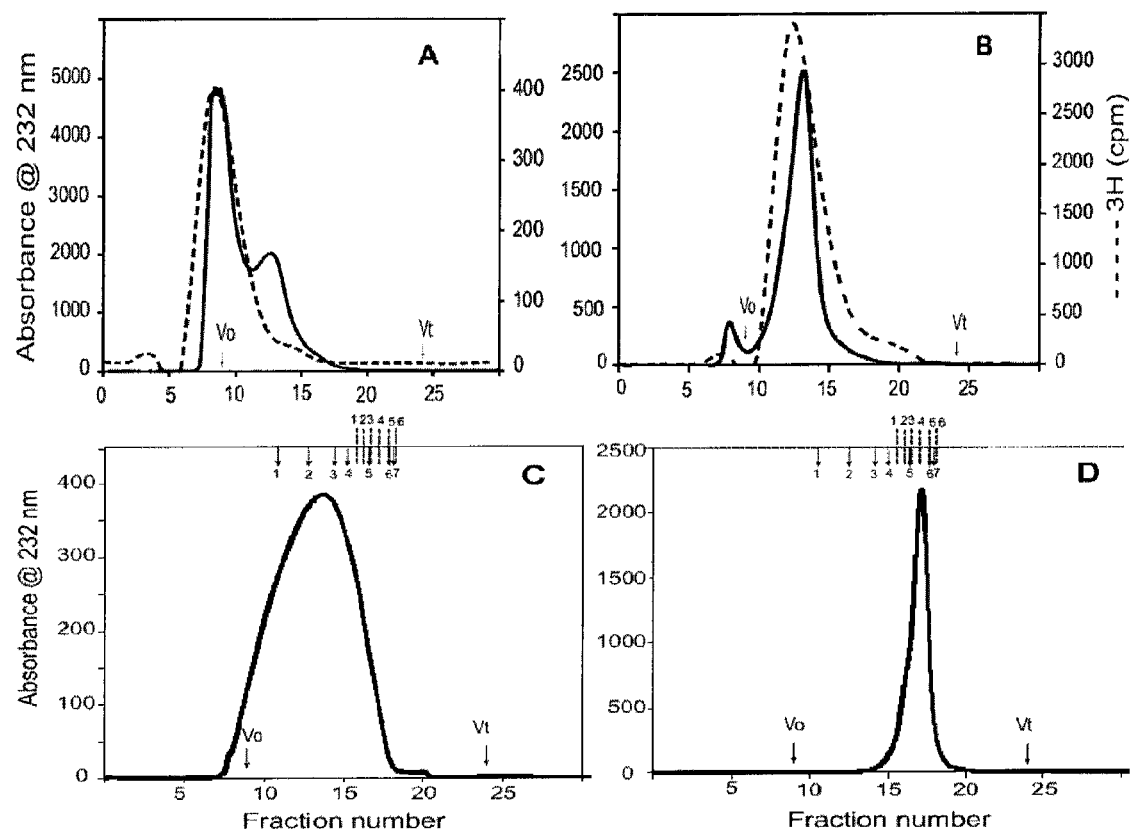
FIG. 1. High performance size-exclusion chromatography of liver heparan sulfates. A Dionex High Performance Liquid Chromatography (HPLC) system was used to equilibrate a prepacked Superdex 75 HR column (10×300 mm, GE healthcare) at 0.5 ml/min in 10 mM HEPES buffer, 150 mM NaCl (pH7.2). The anion-exchange chromatography purified liver HS samples were fractionated to check the intact full chains. Then the high molecular weight 3H labelled male liver HS chains and low molecular weight 3H labeled female liver HS chains were separated and run again on the same column to confirm the homogeneity. The male liver HS (C) and female liver HS (D) were run on the Superdex 200 HR column (10×300 mm) to check the size of the HS chain. The Superdex 200 column was calibrated using gel filtration high and low molecular weight protein calibration marker proteins and even numbered heparin oligosaccharides derived from heparin. The column void (Vo) and total (Vt) volumes were determined using blue dextran 2000 and sodium dichromate, respectively. The elution volumes (Ve) of protein standards were converted into a calibration chart of Kav against molecular mass (Kav=(Ve−Vo)/(Vt−Vo). A line of best fit was fitted to the calibration data using Microsoft Excel, and the equation of this line was used to estimate mass according to observed Kav. The total number of disaccharide repeat was calculated based on the elution position of the known heparin oligosaccharides (dp2-dp26). Completed arrow indicates elution position of HMW and LMW protein standards (1. Ferritin; 2. Aldalose; 3. Conalbumin; 4. Ovalbumin; 5. Carbonic Anhydrase; 6. Ribonuclease A; and 7. Aprotin) and dotted line indicates the elution position of heparin oligosaccharide standards (1.dp26; 2. dp20; 3. dp16; 4. dp12; 5. dp8; and 6. dp6).

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

EXAMPLES

The following experimental Example describes the comparisons of structural and functional properties of mouse gender specific organ heparan sulfate.

We describe analyses of HS chains that were purified simultaneously from the gender specific liver mouse tissues, namely male liver heparan sulfate (MML HS) and female liver heparan sulfate (FML HS) and showed that major gross and fine structural differences exist between male and female liver HS chains. These findings provide further insight into the potential of two differentially sulfated species of HS chains purified from mouse liver tissues to modulate the hMSC proliferation and differentiation. Finally we analyzed the gene expression profile of hMSC during osteogenic differentiation. Our result showed that a set of osteogenic genes are upregulated during hMSC differentiated into osteoblasts. These results demonstrated that differentially sulfated MML HS and FML HS modulate hMSC proliferation and differentiation.

We have applied molecular sieving, enzymatic cleavage and Strong Anion-exchange HPLC methods for structural and composition analyses of intact heparan sulfate chains. The results demonstrated that HS chains purified from gender specific liver tissues are significantly different by a number of parameters. Size determination showed male and female liver intact HS chain length are ~100 kDa and ~22 kDa and comprise 30-40 or 40-50 and 6-8 disaccharide repeats, respectively. This result suggests that the intra-gender specific HS chains show variability across organs. Enzymatic depolymerization and disaccharide composition analyses demonstrated significant differences in domain organization and fine structure between gender specific liver HS. N-unsubstituted Glucosamine (ΔHexAGlcNH$_3^+$, ΔHexA-GlcNH$_3^+$(6S), ΔHexA (2S)-GlcNH$_3^+$, and N-acetyl glucosamine (ΔHexA-GlcNAc) are the predominant disaccharide in male mouse liver HS. However, N-sulfated glucosamine (ΔHexAGlcNSO$_3$) is the predominant disaccharide in female mouse liver HS. We showed that structurally different male and female liver HS exerts a different effect on human mesenchymal cells (hMSC) proliferation and osteogenic differentiation. Finally, the present study demonstrated for the first time that gender specific organ HS chains are distinguishable at the gross and fine structural level, and proved the potential usefulness of gender specific liver HS in modulating hMSC proliferation, osteogenic differentiation and subsequent matrix mineralization.

Materials

Heparin lyase I, II, and III from Flavobacterium heparium, heparin oligosaccharide (dp4-dp26), 12 heparin disaccharide standards and de-O-sulfated and de-N-sulfated heparin oligosaccharides were from Iduron, UK. Chondroitin ABC lyase, neuraminidase, pronase; actinase E, chloroform and methanol were obtained from Sigma-Aldrich (St. Louis, USA). HiPrep 16/10 DEAE columns, HiPrep 26/10 desalting columns, Superdex 75 10/300 GL column, Superdex 200 10/300 GL column and High Molecular Weight (HMW) and Low Molecular Weight (LMW) gel filtration calibration kits were from GE healthcare, Sweden. Bio-Gel P2 was from Bio-Rad Laboratories, Hercules, Calif. Human mesenchymal stem cells (hMSCs) were from Cambrex, USA. All other reagents used were analytical grade. CBA male and female mice of 12-24 weeks old were used in this study. Animals were killed by cervical dislocation, whole liver lobes were loosened from surrounding tissue, and the tissue was cut at the insertion of blood vessels into hepatic hilus to gain all the tissue possible. Harvested livers were rinsed with PBS and immediately frozen and kept in −20° C. until processing.

Tissue Processing, Isolation and Purification of Heparan Sulfate

Liver tissues were cut into small pieces (<1 mm$^3$) and homogenized using a homogenizer. Fat was removed by washing the homogenized tissues with chloroform/methanol mixtures (2:1, 1:1, 1:2 (v/v)). The defatted materials were freeze-dried under vacuum and stored at −20° C. until further use. The dried, defatted tissues were each suspended in 0.05.M Tris acetate buffer (pH 8.0) and digested for 48 h by actinase E 10 mg/g (Sigma) at 50° C. The proteolyzed homogenates were placed in a boiling water bath for 30 min to deactivate the protease and then centrifuged (2500×g) for 30 min at room temperature. The recovered supernatant was passed through a HiPrep DEAE column and total glycosaminoglycans (TGAGs) were eluted with high salt. The eluted samples were desalted using a HiPrep desalting column and freeze-dried. The samples were quantified for the uronic acid content by carbazole method (20). The TGAGs were treated with neuraminidase and chondroitin lyase ABC at 37° C. for 24 h to remove sialic acids, chondroitin and dermaton sulfate. After chondroitinase digestion, the reaction was terminated by heating in a boiling water bath for 15 min and the digested sample were diluted 1:10 times with water. The diluted samples were passed through the HiPrep DEAE column and HS were eluted with high salt. The eluted samples were desalted using a HiPrep desalting column and the resulting HS samples were freeze-dried. The samples were quantified for uronic acid content by carbazole method (20). HS samples were run on a Superdex 75 (10/300) column for sizing of the GAG chains. The Superdex 75 column separated homogenous populations of HS chains were further analyzed on a Superdex 200 column to confirm their sizes. Protein HMW and LMW protein standards (GE healthcare) and even numbered heparin oligosaccharides derived from heparin (highly sulfated) were used to calibrate the sizing column.

Enzymatic Depolymerization of Heparan Sulphate

The purified HS samples were treated with heparinase I, heparinase II or heparinase III. Dried samples (100 μg) were dissolved in 100 mM sodium acetate/0.2 M calcium acetate; pH 7.0 and incubated with 10 mU/ml of heparinase I, or Heparinase II or heparinase III in the same buffer at 37° C. for 16 h and then a second aliquot of enzyme added and incubated for a further 6 h. The heparinase I or heparinase II or heparinase III digested HS samples were analyzed on BioGel P-10 column (1×120 cm) equilibrated with 0.25 M NH$_4$HCO$_3$. Even numbered oligosaccharides derived from heparin were used as standards to calibrate the column.

Disaccharide Analysis Using Strong Anion Exchange Chromatography (SAX-HPLC)

Each sample was sequentially digested for a recovery of disaccharides for SAX-HPLC analysis; for this the samples were digested at 37° C. as follows: heparinase I for 3 h, Heparinase III for 2 h, heparinase II for 16 h, and finally an aliquot of each lyases for 6 h.

Samples were run on a Bio-Gel P-2 column (1×120 cm) equilibrated with 0.25 M NH$_4$HCO$_3$ to recover the disaccharides. The disaccharide products were freeze-dried prior to disaccharide analysis. The constituent of lyase-derived disaccharides were resolved by SAX-HPLC on a ProPac PA1 analytical column (4×250 mm) linked to a Dionex ICS-3000 HPLC system. After equilibration in the mobile phase (double distilled water adjusted to pH 3.5 with HCl) at 1 ml/min, samples were injected and disaccharides eluted with a linear gradient of sodium chloride from 0-1 M over 60 min in the same mobile phase. The elution was monitored for UV absorbance at 232 nm. Disaccharides were identified by comparison with the elution positions of known 12 disaccharide standards from Iduron.

Effect of Male and Female Liver HS on hMSC Proliferation

Human mesenchymal stem cells (hMSCs) (Cambrex, USA) were plated in maintenance medium consisting of DMEM (1000 mg/L glucose), 10% fetal calf serum (FCS), 2 mM L-glutamine and 100 U/ml penicillin-streptomycin sulfate at 37° C. in a humidified atmosphere with 5% $CO_2$. To assess their proliferation, assays were performed to determine cell number utilizing the GUAVA PCA-96 System (GUAVA Technologies) as per the manufacturer's instructions. Briefly, cells were seeded at 3,000 cells/cm$^2$ in 48-well plates and allowed to adhere overnight. The following day the cells were re-fed with the same medium with or without different concentrations of HS (12.5, 1.25, 0.625, 0.312 and 0.156 μg/ml) and the medium were changed every 3 days. Proliferation of cells was assessed by Guava viacount on 1, 3, 5 and 7 day to determine the total viable cells. Cells were washed in PBS, pelleted with 0.125% trypsin, the trypsin neutralized, the pellet resuspended in 400 μl of PBS with the addition of 4 μl of Flex reagent, incubated for 10 min and cell number and viability determined utilizing the GUAVA Viacount software.

HS Binding Assay

The interaction between HS and growth factor was determined using GAG binding plates (Iduron) according to manufacturer's instructions. Briefly, HS was coated on the plate prior to adding growth factors. Bound growth factor was detected using biotinylated antibodies (R&D system).

Effect of Male and Female Liver HS on hMSC Proliferation

Human mesenchymal stem cells (hMSCs) were plated in maintenance medium consisting of DMEM (1000 mg/L glucose), 10% fetal calf serum (FCS), 2 mM L-glutamine and 100 U/ml penicillin-streptomycin sulfate at 37° C. in a humidified atmosphere with 5% $CO_2$. To assess their proliferation, assays were performed to determine cell number utilizing the GUAVA PCA-96 System (Millipore, USA) as per the manufacturer's instructions.

Briefly, cells were seeded at 3,000 cells/cm$^2$ in 48-well plates and allowed to adhere overnight. The following day the cells were re-fed with the same medium with or without different concentrations of HS (12.5, 1.25, 0.625, 0.312 and 0.156 μg/ml) and the medium changed every 3 days. Proliferation of cells was assessed on days 1, 3, 5 and 7 to determine total viable cells. Cells were washed in PBS, pelleted with 0.125% trypsin, the trypsin neutralized, the pellet resuspended in 400 μl of PBS with the addition of 4 μl of Flex reagent, incubated for 10 min and cell number and viability determined utilizing the GUAVA Viacount software.

Cell Lysis and Immunoblotting

MSCs were seeded in designated media at 5,000/cm$^2$ in six-well plates and cultured until subconfluent. Cells were washed and deprived of FCS for 24 h and then treated with HS or FGF-2 alone, or together with the FGFR1-blocking drug SU5402 (Calbiochem) at 10 μm in DMSO for 60 min. Cells were lysed in 300 μL of ice-cold lysis buffer [150 mM NaCl, 10 mM Tris pH 7.4, 2 mM EDTA, 1% Triton X-100, 0.1% sodium dodecyl sulfate (SDS), 0.5% Igepal] supplemented with 0.2 mM sodium orthovanadate, 1 mM phenylmethylsulfonyl fluoride and 30 μL of Protease Inhibitor Cocktail (Sigma). The lysate was incubated on ice for 10 min, passed through a 21-gauge needle and then centrifuged at 10,000 g for 10 min at 4° C. to remove cellular debris. Protein content was determined using a Protein Assay Kit (Bio-Rad) following the manufacturer's instructions. Protein (20 µg) was mixed with an equal volume of 2× Laemmli buffer, boiled for 5 min, and then separated by SDS polyacrylamide gel electrophoresis on 8% gels. The protein was then transblotted onto nitrocellulose membranes (Amersham Biosciences) using a Trans-Blot® SD cell semi-dry transfer apparatus (Bio-Rad) for 15 min at 20 V. The membranes were blocked in 5% nonfat milk in Tris-buffered saline Tween-20 (TBST) (1.5M NaCl, 1M Tris, pH 7.4, 1% Tween) for 1 h and incubated overnight at 4° C. with rabbit anti-actin, rabbit anti-ERK1/2, monoclonal anti-diphosphorylated ERK1/2 (Sigma). The membranes were washed with TBST and incubated for 1 h with anti-rabbit IgG- or anti-mouse IgG-HRP-conjugated secondary antibodies (Southern Biotech, Birmingham, Ala.). Following washes, the membranes were covered with SuperSignal® West Pico Chemiluminescent Substrate (Pierce, Rockford, Ill.) for 5 min then exposed on film.

Effect of Male and female Liver HS on hMSC Osteogenic Differentiation

To confirm the effect of osteogenic potential of male and female mouse liver HS, mineralization assays were performed on triplicate cultures of human mesenchymal stem cells (hMSCs) (Cambrex, USA). The cells were seeded in triplicate at a density of 3000 cells/cm$^2$ in 12 well plates in osteogenic medium (maintenance medium supplemented with 10 nM dexamethasone, 25 µg/ml L-ascorbic acid-2-phosphate and 10 mM B-glycerophosphate) and let them adhere for 24 h. The following day the cells were re-fed with the same medium with or without two different concentrations of HS (1 µg/ml or 300 ng/ml) and grown for 3 weeks and the medium were changed every 3 days. To stain for the accumulation of calcium within the matrix, cell monolayers were washed with PBS×3 and incubated with 4% paraformaldehyde (PFA) for 10 min at room temperature (RT). The monolayers were then washed with double-distilled water (ddH$_2$O)×3, incubated with 1% alizarin red stain for 10 min, washed again with ddH$_2$O×3 and air dried. Images were taken using an Olympus BX51 microscope, DP70 camera, and DPControler software V1.1.1.65. For phosphate nodule staining, cell monolayers were then washed with PBS×3 and incubated with 4% PFA for 10 min at RT. Cell monolayers were then washed with ddH$_2$O×3 and incubated for 30 min in 1% silver nitrate under UV light. The monolayers were then washed with ddH$_2$O×3, incubated with 5% sodium thiosulfate for 2 min and washed again with ddH$_2$O×3 and air dried. Images were taken using an Olympus BX51 microscope, DP70 camera, and DPControler software V1.1.1.65.

Histomorphometry Image Analysis

Bioquant Image Analysis® software (Bioquant Image Analysis Corporation, TN, USA) was used to quantify the average density of Alizarin red S and von Kossa stained wells. Briefly, cultures were performed in triplicate 21 day cultures. MML HS and FML HS treated cultures for each concentration were performed on the same plate. To ensure the same light intensity and exposure within the samples, images of the plates were taken using an Epson Perfection 1670 scanner. Using the image analysis software, the digital images were loaded into the field of view and a consistent region of interest (ROI) was placed over each well. The average density of the wells was recorded for each sample and is reported in units of grayscale. In these measurements, a darker stain correlates with minimal light transmission giving a higher density value. The data is presented as this value subtracted from the value for white light, giving apparent stain signal intensity.

Reverse Transcription—Polymerase chain reaction (qRT-PCR)

Human mesenchymal cells were seeded in triplicate at a density of 3000 cells/cm$^2$ in 12 well plates in osteogenic medium (maintenance medium supplemented with 10 nM dexamethasone, 25 µg/ml L-ascorbic acid-2-phosphate and 10 mM B-glycerophosphate) and let them adhere for 24 h. The following day the cells were re-fed with the same medium with or without two different concentrations of HS (1 µg/ml or 300 ng/ml) and grown for 3 weeks and the medium were changed every 3 days. Total RNA was extracted at day 7, 14 and 21 days using a Nucleospin® RNA II kit according to the manufacturer's instructions (Macherey-Nagel, Easton, Pa.). First strand complementary DNA (cDNA) synthesis was carried out on total RNA using superscript III reverse transcriptase according to the manufacturer's instructions (Invitrogen, Carlsbad, Calif.). Real time PCR primers and probe sets (described in Table 1) for quantitative real-time PCR were designed using Primer Express (Ver. 1.0; Applied Biosystems) and synthesized by Proligo (Proligo LLC, Boulder, Colo.).

Quantitative PCR (qPCR) was then performed to assess the relative expression of the target genes in hMSCs. This was carried out on an ABI Prism 7000 sequence detection system (Applied Biosystems, Warrington, UK) using 600 nmol/l forward and reverse primers, 250 nmol/l probe, and Taqman PCR Master Mix (ABI Applied Biosystems). Reactions were run using the thermal profile; with an initial 10 min activation step at 95° C. followed by 45 cycles of 95° C. for 20 sec; 55° C. for 10 sec, 60° C. for 30 sec and 72° C. for 40 sec. Biological triplicates were measured in triplicates and data were normalized to 18S ribosomal RNA expression in each sample.

RESULTS

Purification and Sizing of Intact Gender Specific Mouse Liver HS Chains

The male and female mouse HS-GAGs chains were isolated using DEAE anion-exchange chromatography. Subsequent separation on Superdex 75 demonstrated that the male liver HS chains eluted a major high molecular weight and a smaller small molecular weight peak (FIG. 1A). In contrast to male, female liver HS chains eluted a major small molecular weight and small high molecular weight peak (FIG. 1B). Thus in each case, the original HS GAG chain preparation was composed of two distinct populations of heparan sulfate chains. We further separated the high molecular weight peak of MML HS and small molecular weight peak of FML HS. We re-ran the separated MML high and FML low molecular weight HS peaks on Superdex 75 column to check the homogeneity. The Superdex 75 separated homogenous population of MML HS and FML HS chains were sodium borohydrate treated to release the linker oligosaccharide from the peptide backbone and fractionated on Superdex 200 columns to determine the size of the HS chains. Separation on Superdex 200 demonstrated that the MML HS eluted with a Kav of 0.31 and the FML HS eluted with a Kav of 0.54 (FIGS. 1C and D). The relative molecular weights of male and female liver HS chains were determined to be 100,000 and 22,000 Da, respectively. In addition to this the Superdex 200 column was calibrated with the available even numbered heparin oligosaccharides from Iduron, ranging from Dp2 to Dp26. The FML HS chains have the same. Kav of Dp12 but the MML HS chains are above Dp26. From these data we concluded that the intact FML HS chain composed of approximately 6-8 disaccharides repeats and MML HS chain is composed of approximately 30-40 or 40-50 disaccharides repeats. The calculated values showed significant variation in chain lengths between MML HS and FML HS.

Enzymatic Depolymerization of HS Chains

Figure 2:
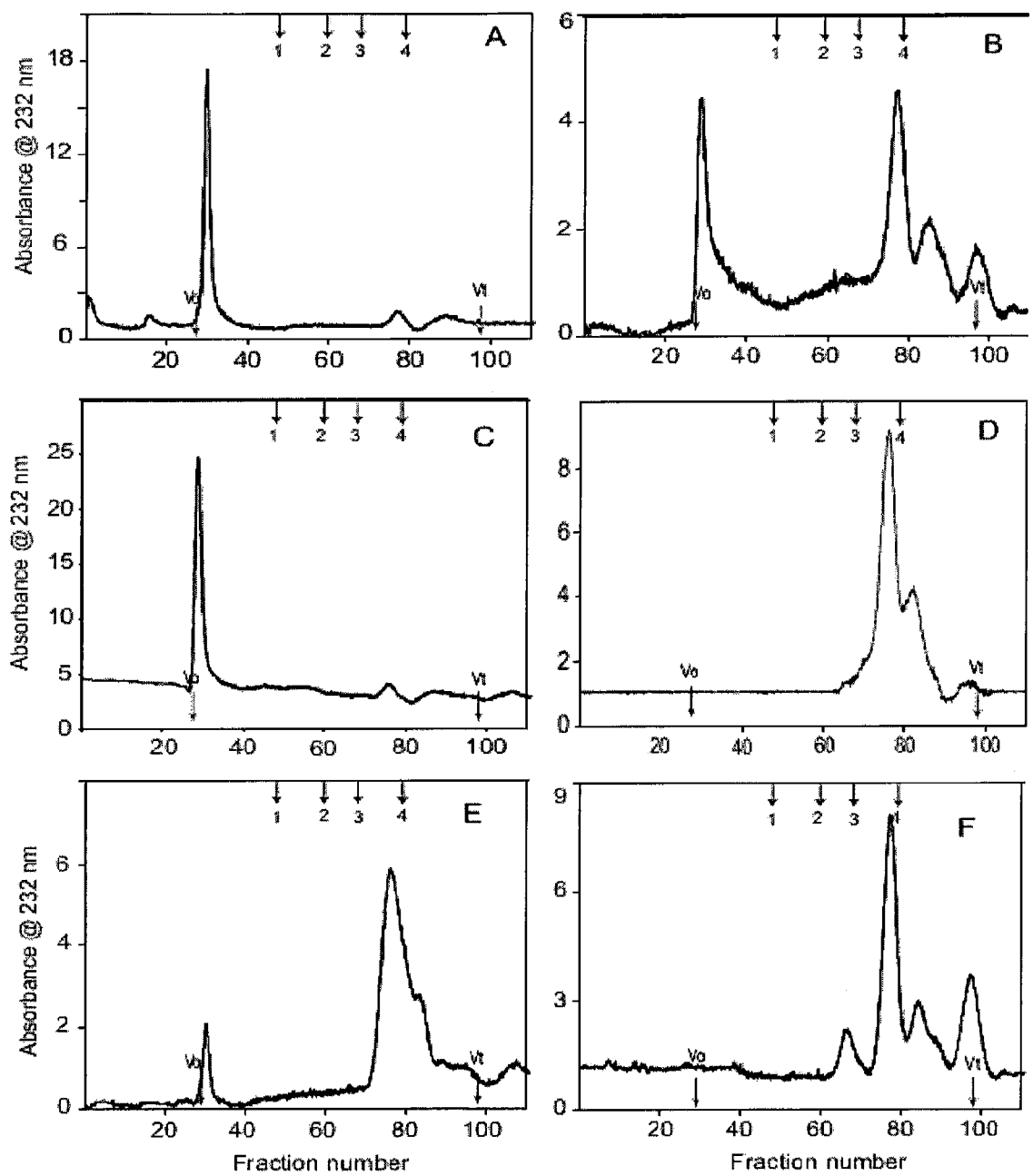
FIG. 2. Bio-Gel P10 size-exclusion chromatography profiles of male and female liver HS after cleavage with heparinase I or heparinase II, or Heparinase III (A) Male liver HS after digestion with heparinase I, (B) Female liver HS after digestion with heparinase I, (C) Male liver HS after digestion with heparinase II, (D) Female liver HS after digestion with heparinase II. (E) Male liver HS after digestion with heparinase III, (F) Female liver HS after digestion with heparinase III. The columns void (Vo) and total (Vt) volumes were determined using haemoglobin and sodium-dichromate, respectively. The column was calibrated using even numbered heparin oligosaccharides derived from heparin. The enzyme digested peaks were identified by the elution position of the known heparin oligosaccharides. The arrow indicates the elution position of heparin oligosaccharide standards (1.p26; 2. dp16; 3. dp10; 4. dp6; 5. dp4; and 6. dp2).

Heparinase treated male and female liver HS were applied to a Bio-Gel P10 column (1×120 cm) to access the distribution and ratios of the resulting oligosaccharides. Representative patterns of the male and female liver HS after heparinase I digestion are shown in FIGS. 2A and B. Digestion by heparinase I was more extensive in FML HS than MML HS. The male liver HS depolymerization profile showed approximately 10% linkages susceptible to heparinase I. There was a corresponding majority of resistant regions of larger size to be excluded from the Bio-Gel P10 column (FIG. 2A). However, the female liver HS depolymerization profile showed 60% linkages are susceptible to heparinase I to yield di- and tetrasaccharides. A correspondingly smaller percentage of resistant regions of larger oligosaccharides are still eluted in the void volume (FIG. 2B). The splitting of the disaccharide peak is due to almost complete resolution of the disaccharides into di- and tri-sulfated. This reflects the small clusters of the heparinase I susceptible sites in the HS chains.

The heparinase II digested MML HS profile was the same as heparinase I digestion (FIG. 2C). On the other hand FML HS completely digested into di and tetrasaccharides and almost no material remained in the void volume (FIG. 2D). Heparinase III digested approximately 80% of the MML HS chains, the resulting digested fragments were mainly di- and tetrasaccharides and a smaller portion still eluted in the void volume (FIG. 2E). The FML HS chains completely digested into di-, tetra-, and hexasaccharides and almost no material remained in the void volume (FIG. 2F). This approach demonstrated a significant gross structural difference between MML HS and FML HS.

Disaccharide Analysis Using Strong Anion Exchange Chromatography (SAX-HPLC)

Figure 3:
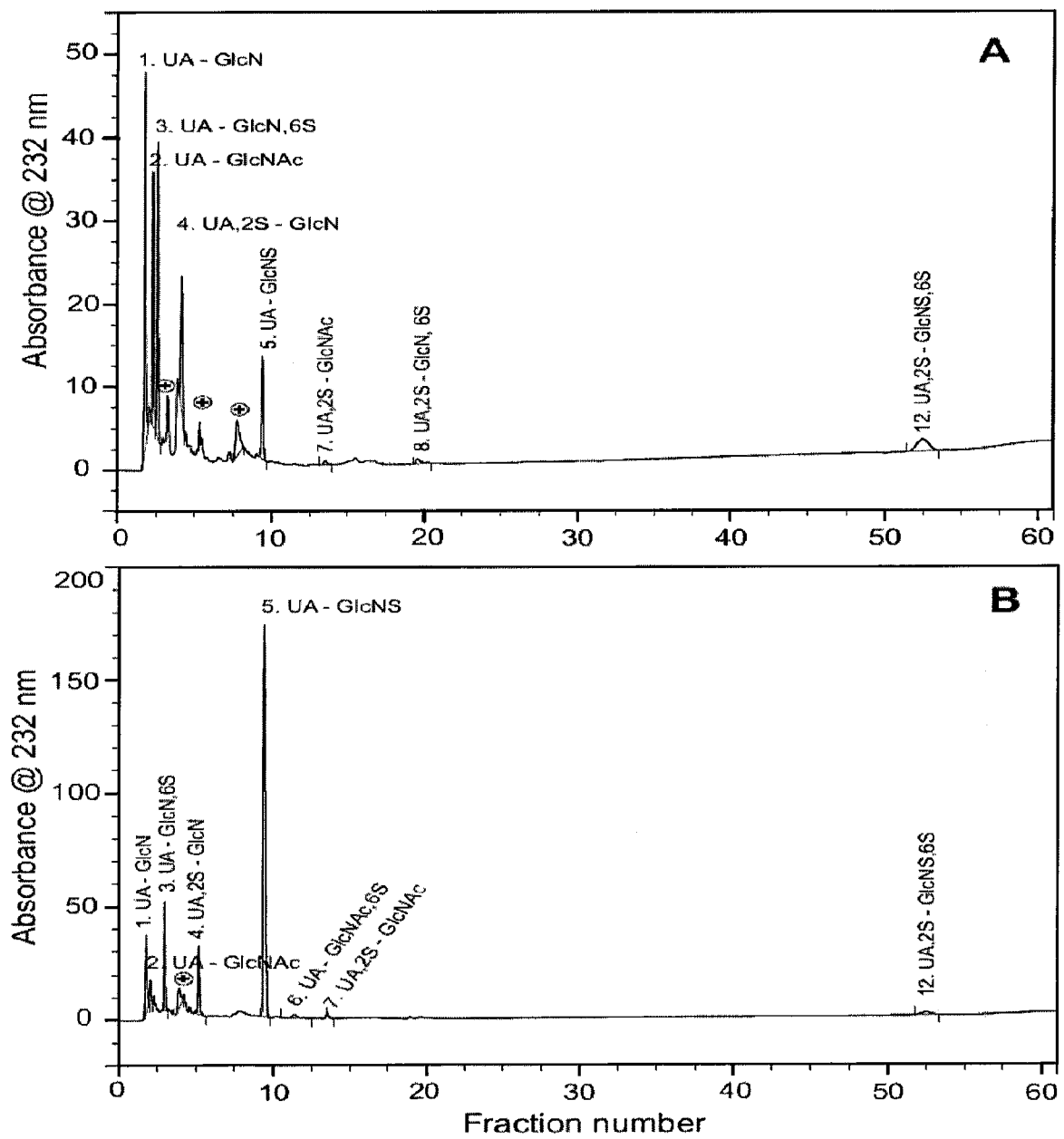
FIG. 3. Strong Anion-Exchange High Performance Liquid Chromatography profiles of male and female liver HS after cleavage with heparin lyases. Disaccharides were prepared by exhaustive digestion with a combination of heparinases I, II and III. Disaccharides were purified by Bio-Gel P2 gel filtration chromatography, and then resolved on a Pro-Pac PA1-SAX-HPLC column eluted with gradient of NaCl as described under Material and Methods. The elution was monitored using a UV detector at 232 nm. (A) Male liver HS after digestion with Heparinase I, II and III and (B) Female liver HS after digestion with heparinase I, II and III. The column was calibrated using 12 unsaturated heparin disaccharide standards from Iduron 1. $\Delta$HexUA-GlcNH$_3^+$; 2. $\Delta$HexUA-GlcNAc; 3. $\Delta$HexUA-GlcNH$_3^+$(6S); 4. $\Delta$HexUA (2S)-GlcNH$_3^+$; 5. $\Delta$HexUA-GlcNSO$_3$; 6. $\Delta$HexUA-GlcNAc (6S); 7. $\Delta$HexUA(2S)-GlcNAc; 8. $\Delta$HexUA(2S)-GlcNAc (6S); 9.$\Delta$HexUA(2S)-GlcNH$_3^+$(6S); 10. $\Delta$HexUA(2S)-GlcNSO$_3$; 11, $\Delta$HexUA-GlcNS(6S), 12. $\Delta$HexUA(2S)-GlcNS(6S). The number on the peak corresponds to the elution position of known disaccharide standards.
Figure 4:
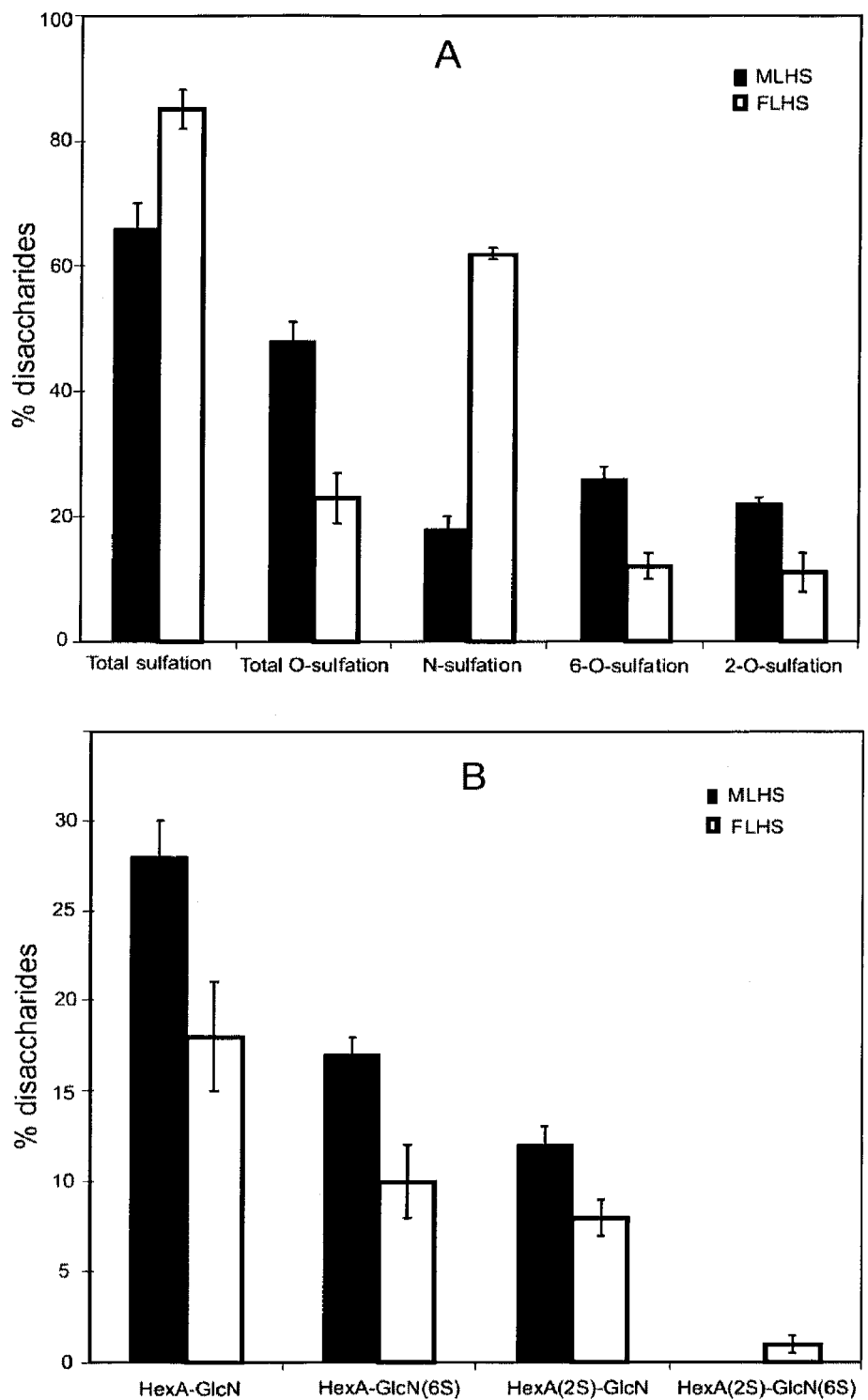
FIG. 4. The percentage composition of sulfated and N-unsubstituted disaccharides of male and female liver tissues analyzed by SAX-HPLC. (A) The percentage of total, O-, N-, 6-O- and 2-O-sulfated disaccharides among total disaccharides of male and female liver HS. (B) The percentage of N-unsubstituted disaccharides among total disaccharides of male and female liver HS. Growth factors binding to male and female mouse liver HS. Growth factors binding ability of male (C) and female (D) mouse liver HS coated on an Iduron Heparin/GAG binding plates.
Figure 4:
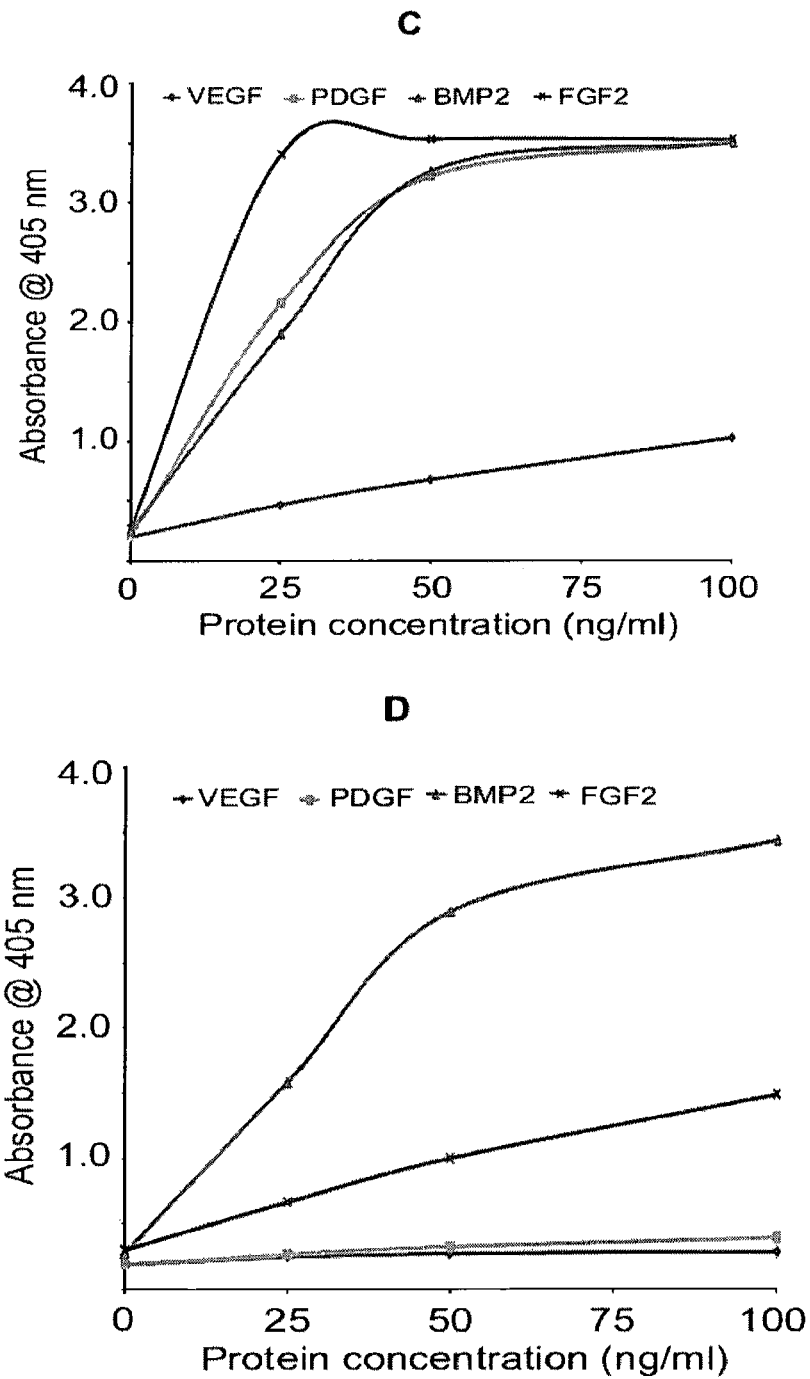

The fine structural differences in the disaccharide content of the male and female liver HS chains were analyzed after exhaustive digestion with a mixture of heparinases I, II and III and separation on Bio-Gel P2 column (1×120 cm), followed by strong anion-exchange HPLC. The resulting disaccharide peaks were identified by reference to well characterized disaccharide standards from Iduron. The SAX-HPLC separated MML HS and FML HS disaccharide profile was shown in FIGS. 3A and B. The area under each peak was used to obtain the disaccharide composition of each sample. Comparisons of the male and female liver HS showed that, N-unsubstituted $GlcNH_3^+$ ($\Delta HexUA-GlcNH_3^+$, $\Delta HexUA-GlcNH_3^+(6S)$, $\Delta HexUA(2S)-GlcNH_3^+$) and N-acetylated ($\Delta HexUA-GlcNAc$) are the predominant disaccharide in the MML HS. However, N-sulfated ($\Delta HexUA-GlcNSO_3$) is the predominant disaccharide in the FML HS (Table 2). The SAX-HPLC data showed a great distinction between the two heparan sulfates in that the MML HS total sulfation was 66% with 18% N-sulfation, 26% 6-O-sulfation and 22% 2-O-sulfation and the FML HS total sulfation was 85% with 62% N-sulfation, 12% 6-O-sulfation and 11% 2-O-sulfation (FIG. 4A). MML HS and FML HS was composed of 57% and 30% N-unsubstituted disaccharides, respectively. This is higher than the 1.2 to 7.5% previously reported with various porcine, bovine and rat tissues (21, 22). Non-sulfated, mono-sulfated and di-sulfated N-unsubstituted disaccharides ($\Delta HexUAGlcNH_3^+$, $\Delta HexUA-GlcNH_3^+(6S)$, $\Delta HexUA(2S)-GlcNH_3^+$ and $\Delta HexUA(2S)-GlcNH_3^+(6S)$) have been detected in both male and female liver HS with different percentages (FIG. 4B). These results demonstrated major structural differences between gender specific liver HS chains at the gross and fine level. GAG binding plates revealed that male liver HS binds to all growth factors tested (FGF2, BMP2, PDGF and VEGF; FIG. 4C) whereas female live HS selectively bound only FGF2 and BMP2 (FIG. 4D).

Effect of Gender Specific Liver HS on hMSC Proliferation

Figure 5:
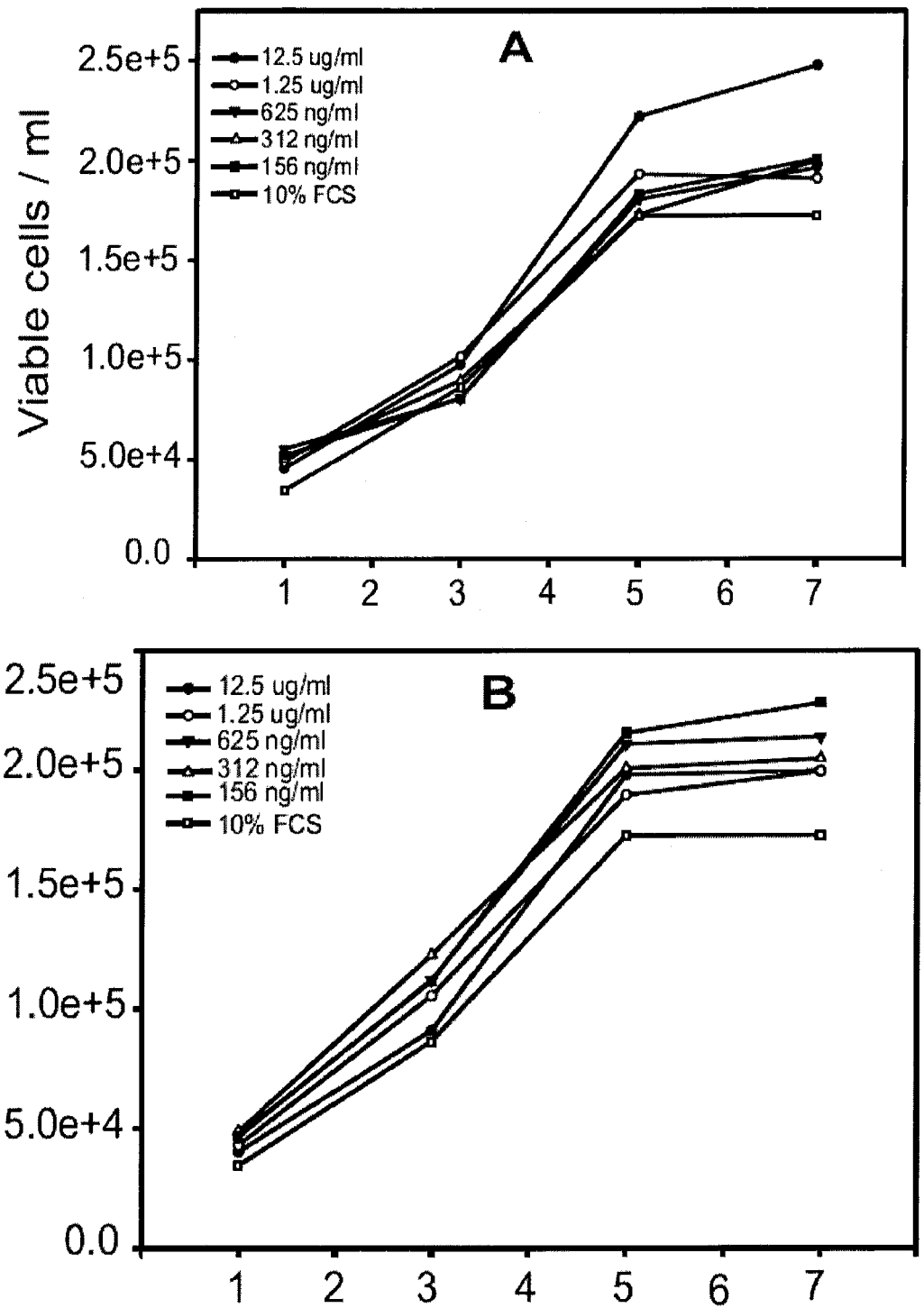
FIG. 5. Effect of male and female liver HS on the growth of hMSC in maintenance and osteogenic medium. Cells were cultured for 7 days in normal maintenance medium in the presence of different concentrations (12.5 µg/ml or 1.25 µg/ml or 625 ng/ml or 312 ng/ml or 156 ng/ml) of male liver HS (A), and female liver HS (B). Cells were cultured for 7 days in osteogenic medium in the presence of different concentrations (12.5 μg/ml or 625 ng/ml or 312 ng/ml) of male liver HS (C), and female liver HS (D). Viable cell counts were determined at day 1, 3, 5 and 7. (E) The importance of FGFR signaling for HS activity was investigated by supplementing serum starved sub confluence cultures with male or female. HS (2.5 μg/ml) or FGF2 (2.5 ng/ml) in the presence or absence of an FGFR1 inhibitor (SU5402 at 20 μM) for 60 min. Total protein was extracted for Western blotting and first probed for activated ERK1/2 expression (pERK1/2). Membranes were then striped and reprobed with anti ERK1/2 antibody. (F) The amount of pERK1/2 protein was determined by densitometry. (G) Cells were cultured for 5 days with male HS (2.5 μg/ml) or FGF2 (2.5 ng/ml) in the presence or absence of an FGFR1 inhibitor (SU5402 at 20 μM).
Figure 5:
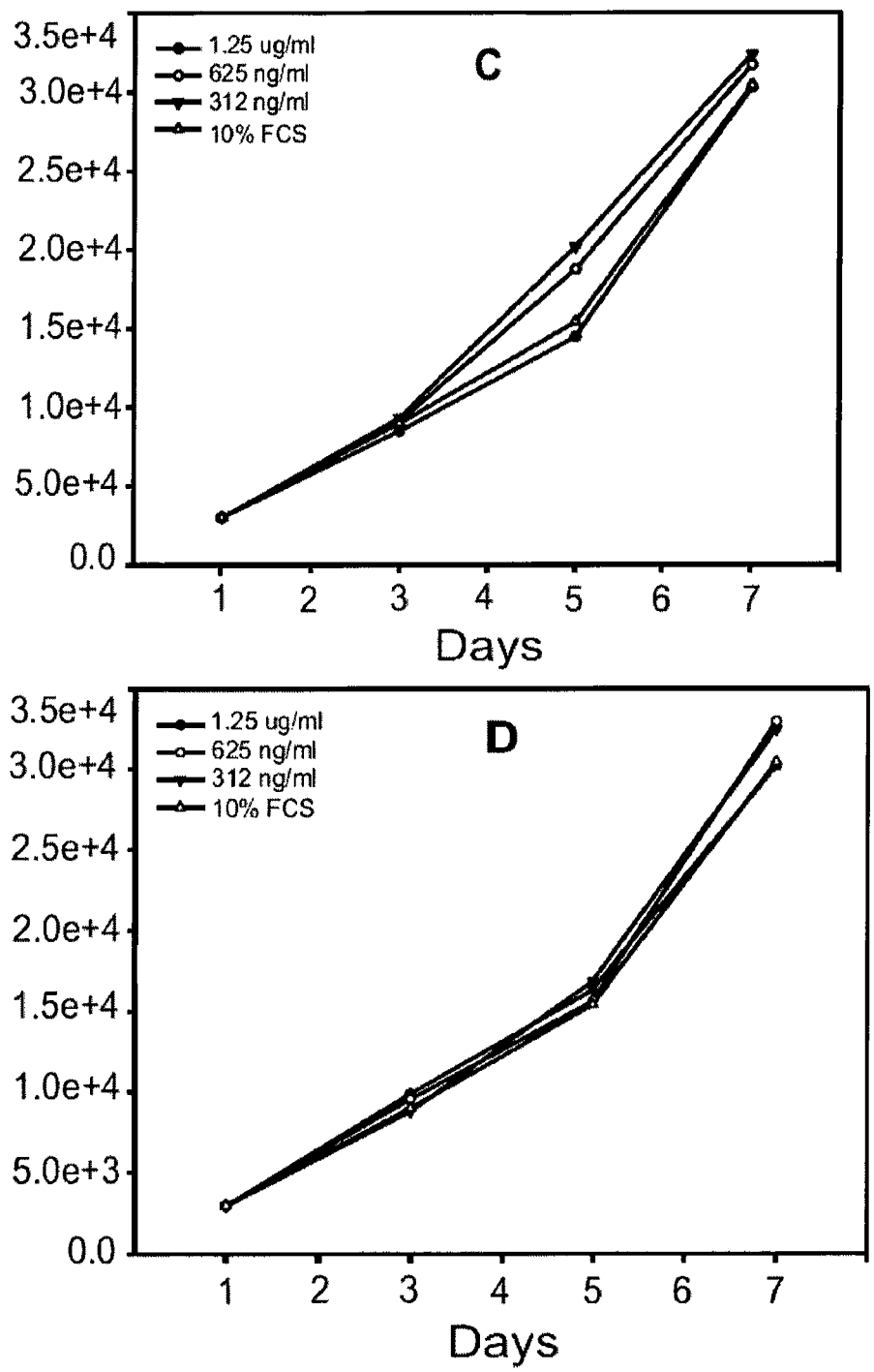
Figure 5:
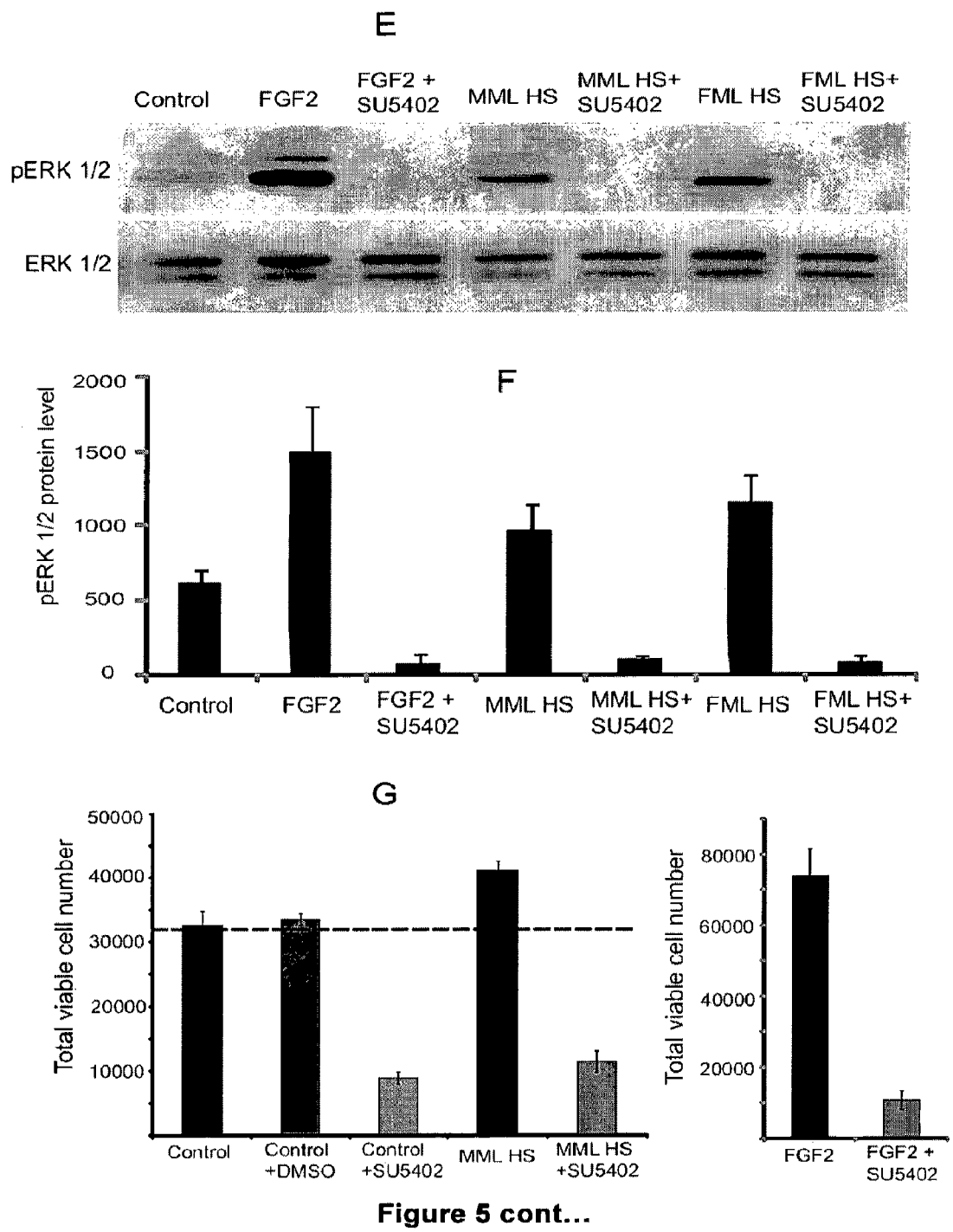

To assess the possibility of structural differences identified between the male and female liver HS to modulate hMSC proliferation, hMSCs were treated with varying concentration of HS and viable cell number was counted over a 7-day culture period in normal maintenance or differentiation (osteogenic) medium. In growth medium, MML HS dose dependently increased the cell number, the highest cell number was obtained with the highest concentration of HS (12.5 µg/ml). However, FML HS at lower concentration (152 ng/ml) increased the highest cell number and higher concentrations gave a relative decrease in the cell number (FIGS. 5A and B). However, in contrast to the maintenance medium, MML HS at lower concentration (312 ng/ml) in the osteogenic medium increased the highest cell number, and FML HS at a higher concentration (12.5 µg/ml) increased the highest cell number (FIGS. 5C and D).

Figure 11:
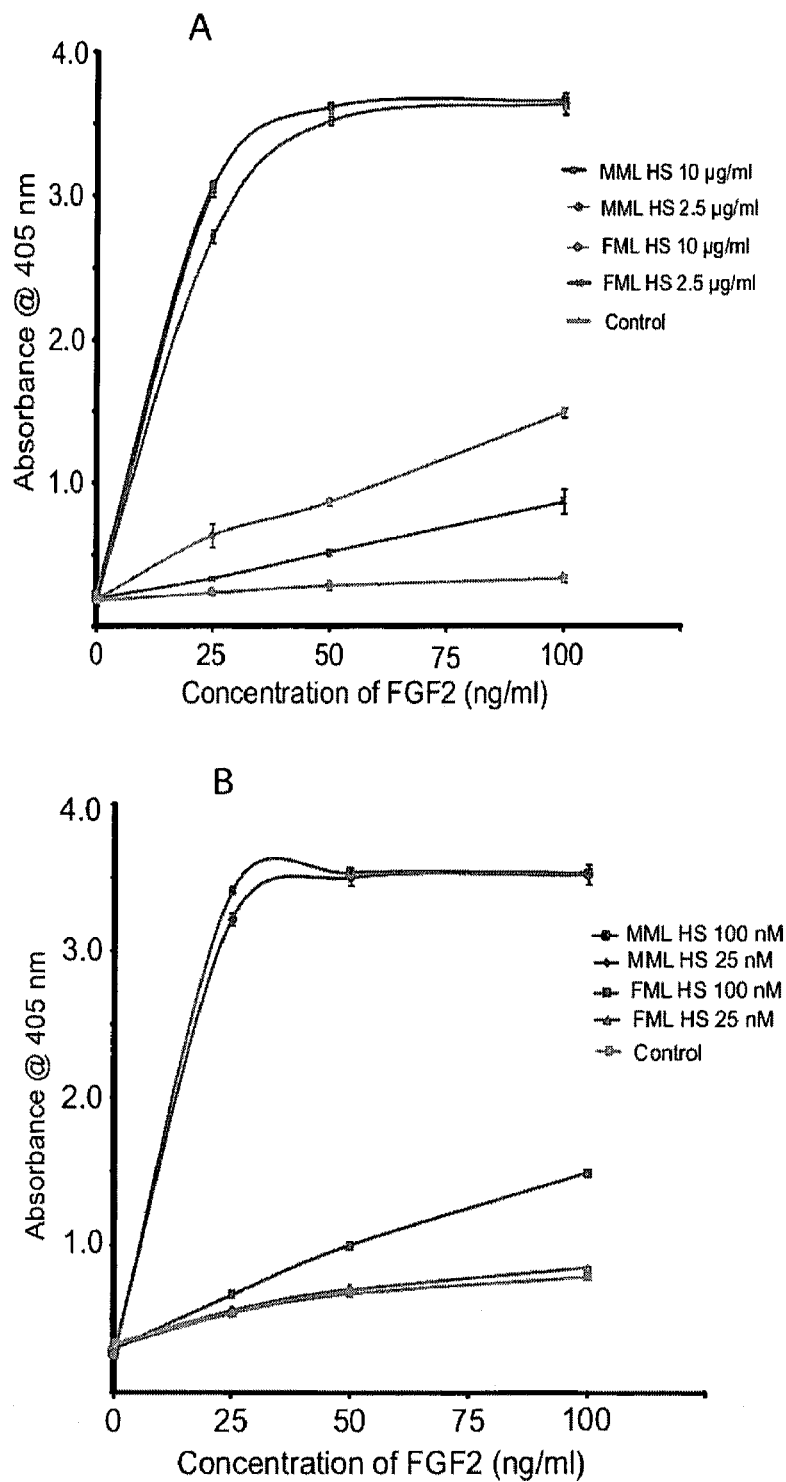
FIG. 11. Growth factors binding to male and female mouse liver HS. (A-E) Growth factors binding ability of male and female mouse liver HS coated on an Iduron Heparin/GAG binding plate. (A) different concentrations of male and female liver HS binding with FGF2, (B) different molar concentrations of male and female liver HS binding with FGF2, (C) different molar concentrations of male and female liver HS binding with BMP2, (D) different molar concentrations of male and female liver HS binding with PDGF BB, (E) different molar concentrations of male, and female liver HS binding with VEGF.
Figure 11:
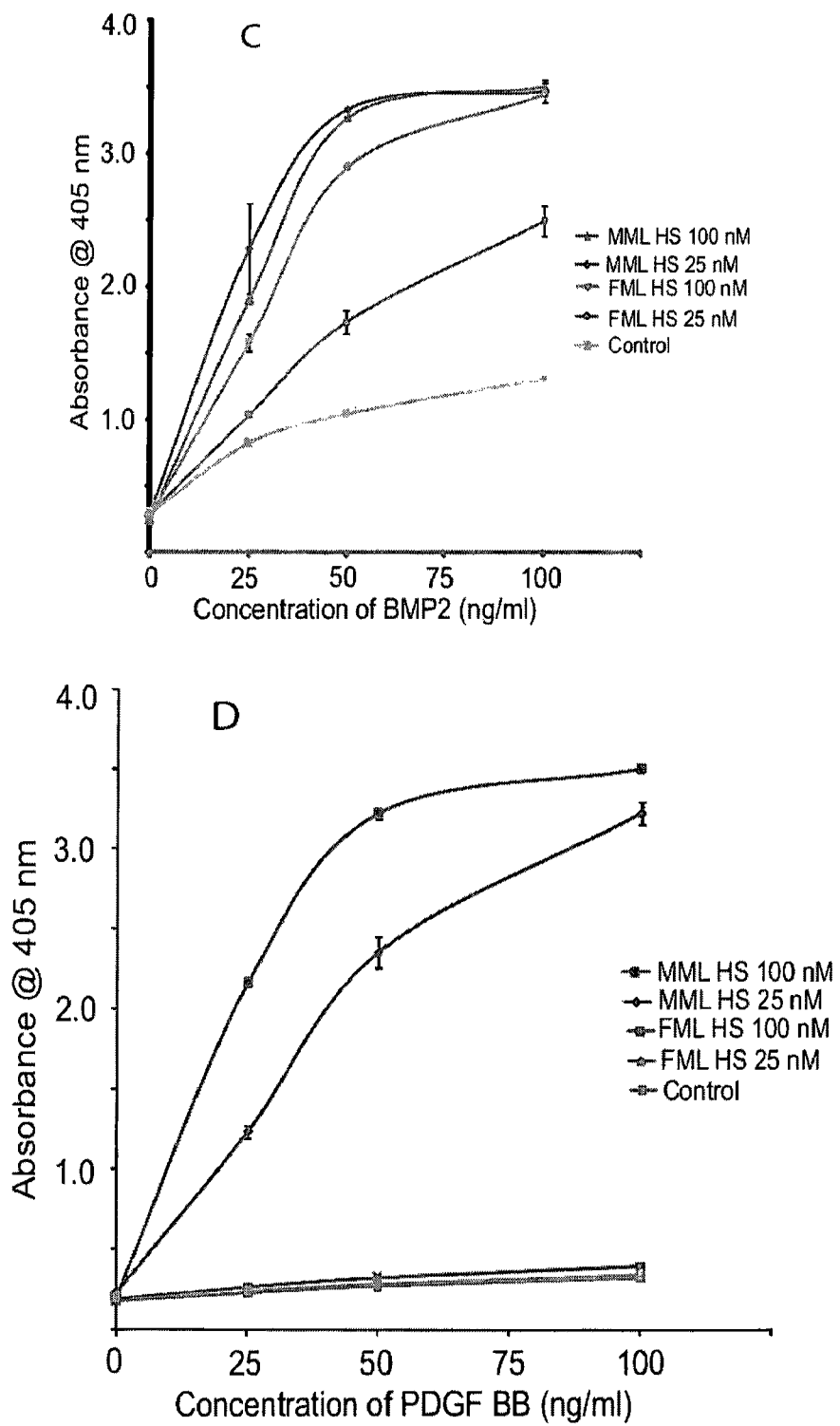
Figure 11:
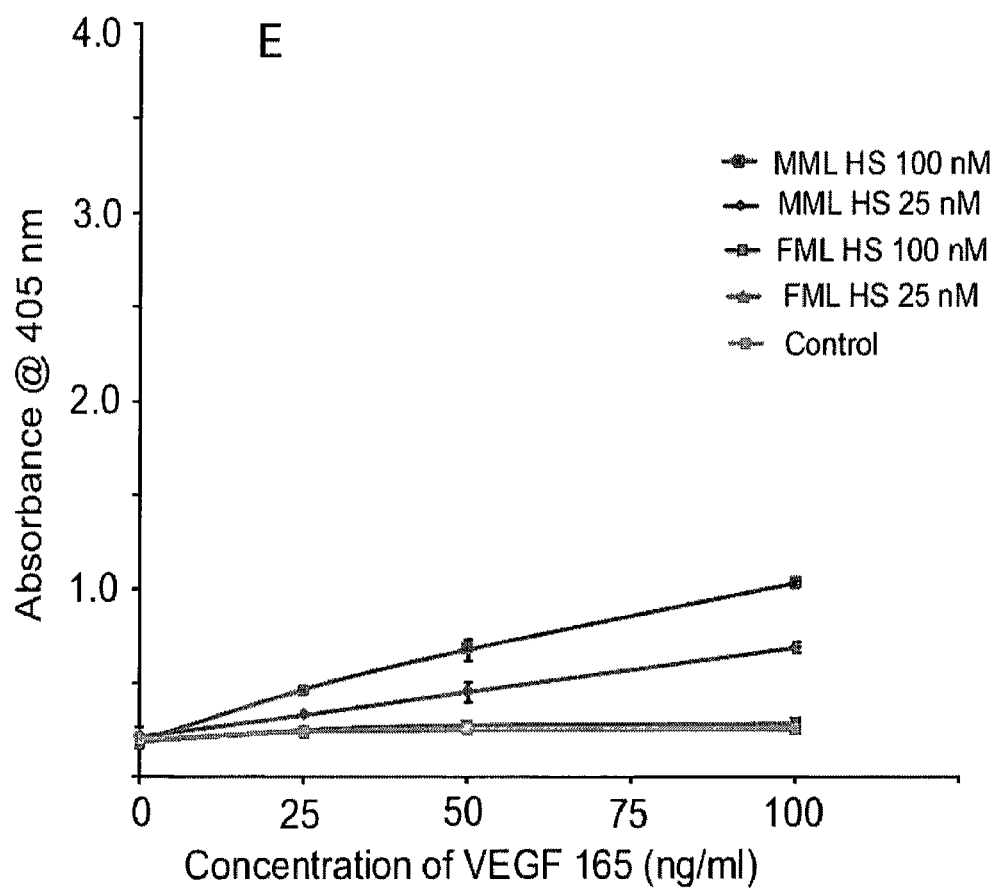

Notably for FML HS, there was an inverse relationship with decreasing doses giving a greater proliferative effect (FIGS. 5A&B). In all cases, liver HS irrespective of gender, stimulated proliferation of hMSCs in the presence of 10% FCS. Taken separately, FML-HS was maximally proliferative at 156 ng/ml, whereas MML-HS was maximally proliferative at 12.5 µg/ml. Notably, despite this dosing effect, both HSs produced similar numbers of hMSCs over a 7-day period ($2-2.5\times10^5$). The GAG-binding plates suggested that the liver HS isolates had much greater affinities for FGF2 than PDGFBB, VEGF165 or BMP2, factors known to be physiologically relevant for hMSCs (FIG. 11). In order to confirm whether the mechanism involved in triggering the proliferation by the liver HS was via FGF2, as HS is a co-receptor for the FGF/FGFR complex and as FGFR1 is a high affinity receptor for FGF-2 binding, we next sought to verify whether the inhibition of this receptor with the chemical inhibitor SU5402 could affect liver HS's intracellular signalling activity. Activation of the ERK cascade is required for FGF-induced mitogenesis. Thus we sought to verify if liver HS, like FGF-2, could induce ERK activation in low serum conditions. As expected if the HS was involved directly with FGFR1, both male and female HS were able to stimulate the phosphorylation of ERK1/2 (FIG. 5E, with protein levels quantified in 5F); the effects for both liver HS species could be blocked with the SU5402. Knowing that MML HS maximally binds FGF2 and increased hMSC proliferation, we next examined whether this effect was mediated by FGFR signaling. Pulsing with SU5402 had an inhibitory effect on the basal growth of hMSCs while also preventing HS and FGF2 induced proliferation (FIG. 5G). This result further confirmed that the mechanism involved in triggering the proliferation by the liver HS was via FGF2/FGFR signaling.

In Vitro Osteogenic Differentiation and Mineralization of hMSC

Figure 6:
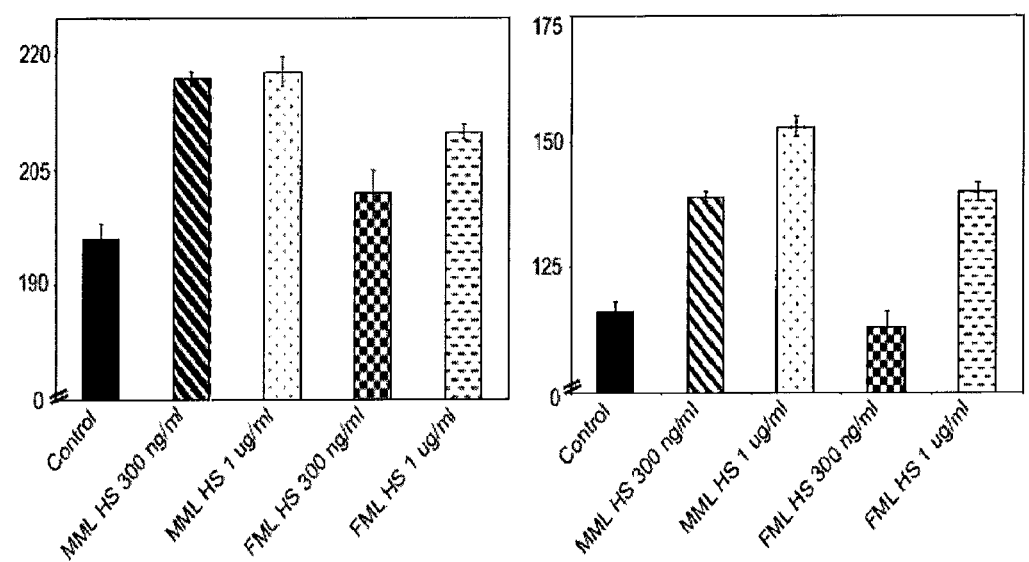
FIG. 6. Osteogenic differentiation of human mesenchymal stem cells (hMSC) 21 days after induction with osteogenic medium. (A) Phase contrast morphology of human mesenchymal stem cells (hMSC) grown in osteogenic medium with or without (300 ng/ml or 1 μg/ml) liver HS after 21 days culture period. All pictures are shown in 10× magnification. (B) Mineralized nodules formed by controls and HS treated hMSC were stained with Alizarin red S and Von Kossa. Representative dishes of different concentration of HS on hMSC at 21 days cultured were stored. (C) Quantitative analysis of Alizarin red S and Von Kossa staining density was measured with BioQuant software. Representative examples of triplicate wells are shown.

We showed that structurally different male and female liver HS exerts a different effect on hMSC proliferation in maintenance and osteogenic medium. Next we examined whether these effects could still be observed when the cells were induced to differentiate down the osteoblast lineage. Photomicrography showed the osteogenic differentiation of hMSC with or without liver HS in osteogenic media for 21 days (FIG. 6A). Our results clearly show that male and female liver HS increases hMSC mineralization in dose dependent manner. MML HS at lower concentration (300 ng/ml) induces high mineralization equal to the higher concentration (1 µg/ml) of FML HS. The effect of liver HS on the osteogenic differentiation of hMSC to mineralize in vitro can be visualized by Alizarin red S and von Kossa staining. MML HS at 300 ng/ml and 1 µg/ml after 21 days, an extensive mineralization noted. FML HS at 300 ng/ml concentration did not show increased mineralization as compared to control and MML HS. But at 1 µg/ml female liver HS increased mineralization equal to 300 ng/ml MML HS. Female liver HS at 300 ng/ml was almost equal to control (FIG. 6B). Measurement of calcium-bound Alizarin red S dye showed higher calcium accumulation in male HS treated samples than MML HS (FIG. 6C). Measurement of mineralized bone nodules by von Kossa staining showed higher bone nodules in MML HS treated cells than FML HS (FIG. 6C).

Expression of Osteogenic Markers

Figure 7:
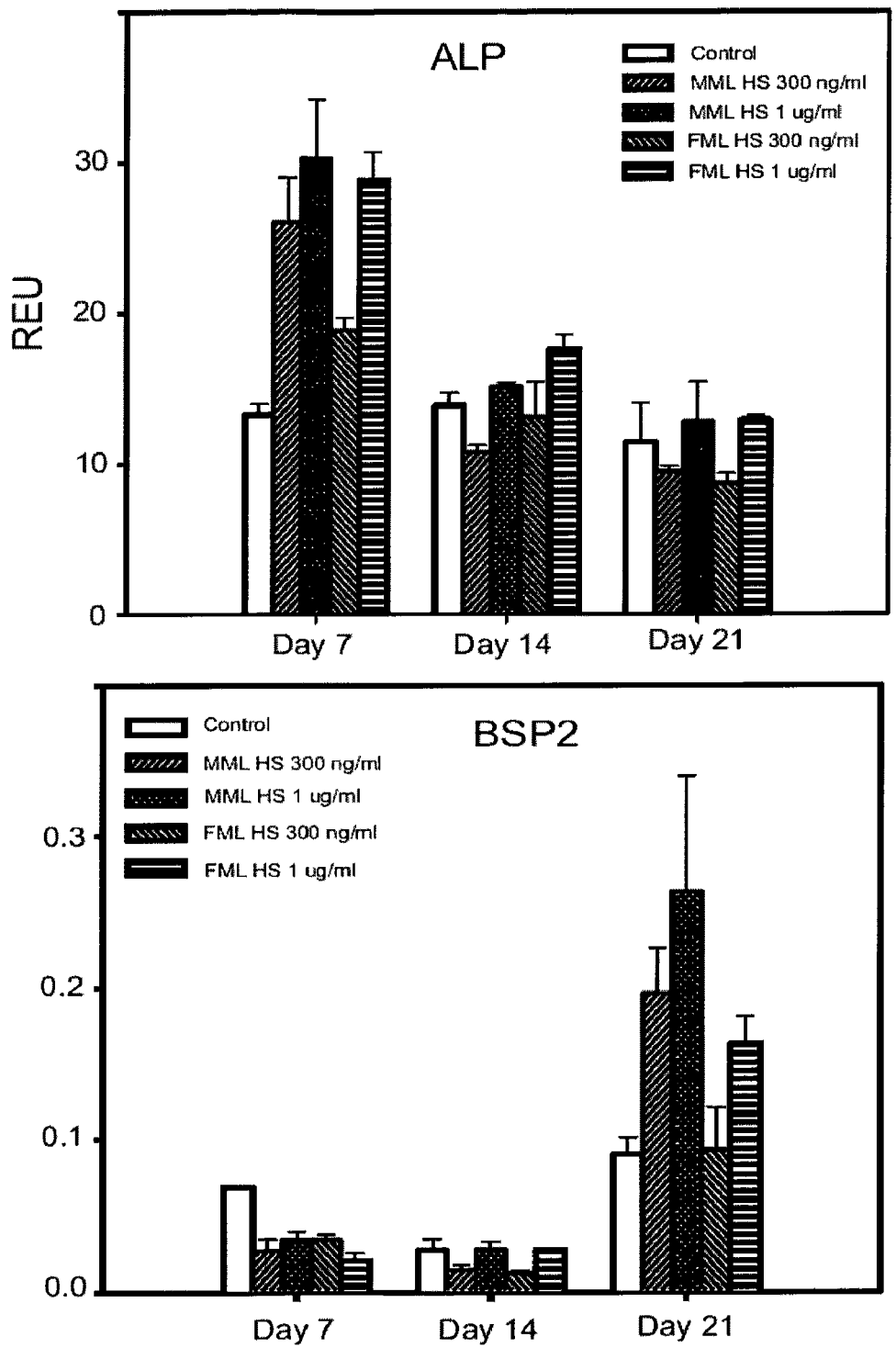
FIG. 7. The expression profile of osteogenic marker genes after 7, 14 and 21 days HS treatment. Human mesenhymal cells (hMSC) were seeded at 3000 cells per cm² and grown in osteogenic medium with or without liver HS for 21 days with medium changes every 3 days. Total RNA was extracted at day 7, 14 and 21, and quantitative real-time polymerase chain reaction was performed using sequence specific primers (Table 1) and probes as markers of osteoblast differentiation. The expression levels of osteogenic markers alkaline phosphatase (ALP), bone sialoprotein 2 (BSP2), osteopontin (OPN) and Runx2 were normalized to universal 18s ribosomal RNA. The data represent mean REU±SEM (n=3).
Figure 7:
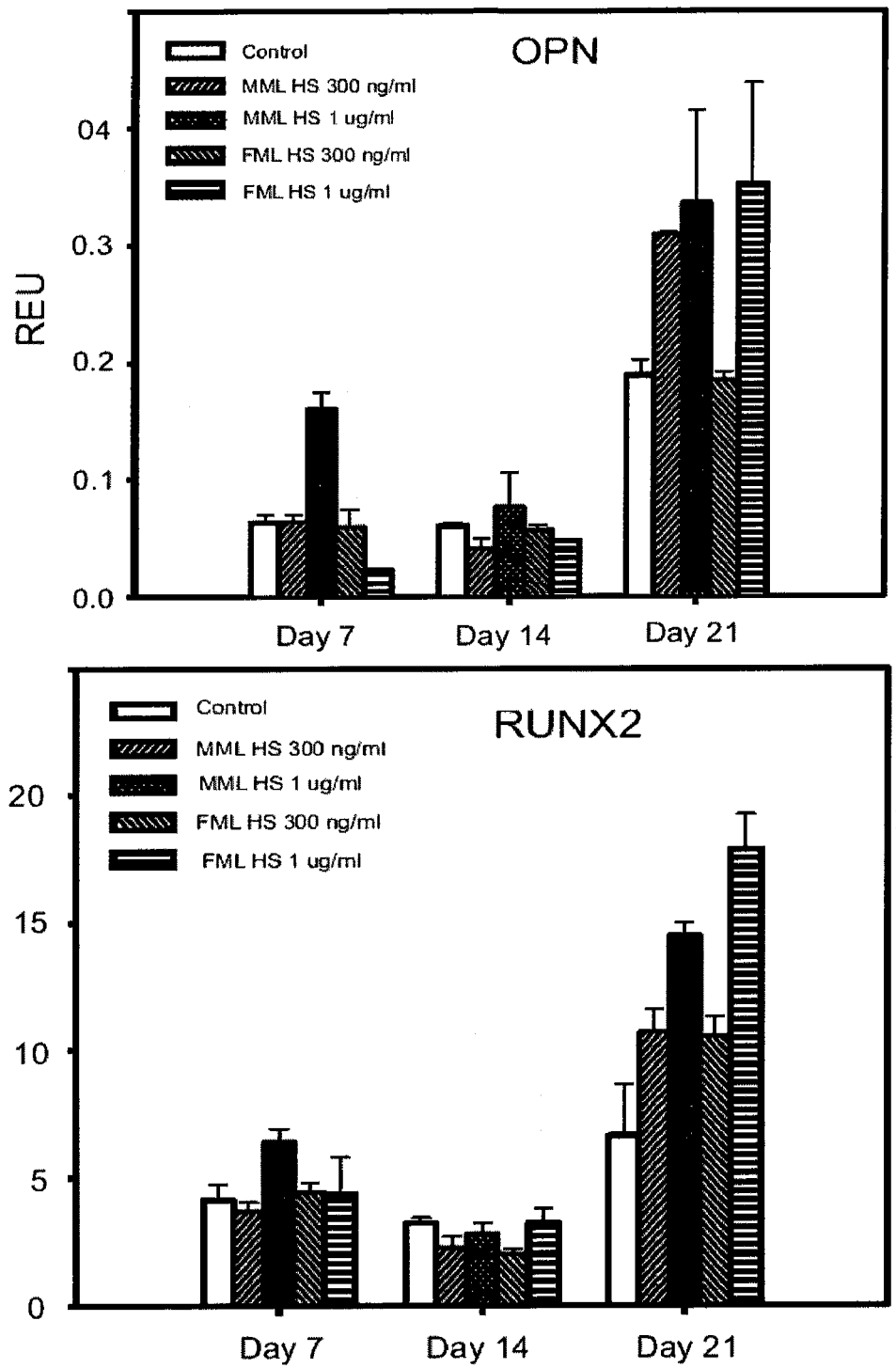

We next investigated the effect of liver HS on the expression of mRNA transcripts related to osteoblast differentiation using qPCR. The expression levels of alkaline phosphatase (ALP), an early transcription factor essential for osteoblast differentiation was markedly increased at the 7 day culture period. The MML HS at 300 ng/ml or 1 µg/ml treated cells showed higher expression of ALP when compared to control. FML HS at higher concentration (1 µg/ml) upregulated ALP expression to become comparable with 300 ng/ml MML HS. In MML HS treated hMSC the expression levels of bone sialoprotein (BSP2), osteopontin (OPN) and Runx2 late transcription factors essential for osteoblast differentiation were upregulated at both concentrations tested over the 21 day culture period compared to controls. On the other hand, the expression of these markers was significantly upregulated at higher concentration 1 µg/ml of FML HS treated hMSC, which is comparable to lower concentration (300 ng/ml) of MML HS treated cells (FIG. 7). The present morphological and genetic results demonstrate that gender specific liver HS differentially modulate osteogenic differentiation of hMSC.

DISCUSSION

HS biosynthesis is a complex multi-step process that occurs in a very specific and sequential manner via membrane-bound enzymes in the endoplasmic reticulum and Golgi apparatus. Heparan sulfate is a ubiquitous component of the extracellular matrix in a wide variety of animal species and tissues. The fine structure of the chains depends on the regulated expression of multiple biosynthetic enzymes, such as glycosyltransferases, sulphotransferase and an epimerase. Structural differences and the presence of N-unsubstituted amino groups were observed in the heparan sulfates from different tissues and species (19, 21, 22). In this study we describe the detailed analysis of the structural and functional properties of the HS chains purified from male and female mouse liver tissue. The results presented suggest the existence of two distinct and separate populations of heparan sulfates. They are structurally different, changes that could be construed to be significant as they could be confirmed at the functional level.

Glycosaminoglycans are linear, sulphated, negatively charged polysaccharides that have molecular weights of roughly 10-100 kDa (23). The SEC-HPLC data showed that the relative molecular weight of MML HS was 100 kDa and intact HS chain size was approximately 30-40 or 40-50 disaccharide repeats, which is comparable to the HS chain length observed from seven rat tissues (21). The FML HS had an apparent molecular weight of 22 kDa and intact HS chain was approximately 6-8 disaccharide repeats. This is consistent with the previous report that, fully sulfated heparin 12 mer (dp12) showed the same molecular mass of 22 kDa (24). We purified HS from different age groups of male and female mouse liver tissues (data not shown), and they all gave the result shown in FIG. 1. This confirmed that HS chain size and structure was gender specific and not dependent on the age of the tissue.

Glycosaminoglycan degrading enzymes Heparinase I, II and III are useful analytical tools for investigating the composition and structural sequence of various HS chains and each heparinase has distinct substrate specificities (25). Heparinase I has high specificity for highly sulfated disaccharides and cleaves HS chains with sulfate-rich regions at an N-sulfated glucosamine/sulfated-iduronic acid (GlcNS ($\pm$6S)-IdoUA(2S)) (26-30). The size of the fragments generated, compared to the undigested chain gives, therefore, the frequency of these areas of high sulfation. Separation of the HS chains from male and female liver HS after digestion with heparinase I gave different profiles. MML HS showed less sensitivity to heparinase I, this reflects that there is no close proximity of heparinase-susceptible sites in the male liver HS which probably exist in relatively small clusters and at the non-reducing end. This is similar to the result obtained with skin HS, the IdoUA residue essential for heparinise I action is present in lower concentrations (6.5-10% of total HexUA) (31-33). Female liver HS showed high sensitivity to heparinase I, with ~65% of the linkages cleaved to yield dp2-dp6 as the major product and 35% yield longer oligosaccharides. This reflects a closer proximity of heparinase-susceptible sites in FML HS than in MML HS.

In contrast to heparinase I, heparinase III cleaves HS chains in N-acetylated or N-sulfated disaccharides regions (GlcNAc/GlcNS-HexA) with a preference for GlcA over IdoA. It will tolerate 6-O sulfation of the amino sugar but is inhibited by 2-O sulfation of IdoA (34, 35). Heparinase III also cleaves non-sulfated, N-unsubstituted disaccharide (GlcA-GlcNH$_3^+$) (36). Heparinase III cleaved 80% of material from MML HS into di- and tetrasaccharide units. This is similar to the 78% obtained for endothelial HS (37) but substantially less than the 63% disaccharide result obtained with skin fibroblasts (31). However, female liver HS was completely degraded into di- and tetrasaccharides. This is unique when compared to other previous HS studied. The susceptible sites were highly contiguous, and the resistant fragments alternated to form tetrasaccharides. These results suggest that FML HS is composed of mostly N-acetylated, N-sulfated and N-unsubstituted disaccharide. Heparinase II has broad substrate specificity (27, 35, 38) and particularly it has two distinct active sites, one of which is heparinase I like, whereas the other is heparinase III like (39). Heparinase II also has substrate specificity on unsaturated disaccharides that are O-sulfated at C2 of uronic acid or C6 of GlcNH$_3^+$(40). MML HS showed less sensitivity, while FML HS showed high sensitivity to heparinase II. This reflects the close proximity of heparinase II susceptible sites in FML HS. The specificity of individual heparinase analyses of the male and female HS showed both to have a distinctive structure and composition.

Disaccharide composition analyses showed MML HS is less sulfated than FML HS. This is consistent with the heparinase I digestion profile of MML HS and FML HS (FIGS. 2A and B). Comparing male and female liver HS it can be seen that $\Delta$HexUA(2S)-GlcNS(6S) and $\Delta$HexUA-GlcNS are the most likely to be the non-reducing end sulphated disaccharides for both HS. This finding is consistent with the previous report that the non-reducing end of bovine kidney HS is heavily sulfated and especially N-sulfated (41). MML HS showed ~70% disaccharides were less sulfated, but heparinase II digestion produce only ~10 disaccharides, this is because the N-acetylated saccharides (GlcAGlcNAc) continuously present in the reducing end are cleaved into disaccharides, but the N-sulfated, N-unsubstituted and 6-O-N-unsubstituted saccharides present on the N-acetyl/N-sulfated region in the middle of the HS chain. This enzyme cleaves these saccharides, because of the longer chain length with concomitant higher mass it was excluded in the void volume of the BioGel P10 column (FIG. 2C). However, in FML HS ~90% saccharides were less sulfated, so the complete chain was cleaved by Heparinse II to make disaccharides (FIG. 2D). This reflects the close proximity of heparinase II susceptible sites in the whole FML HS chains. MML HS heparinase III digestion produced ~80% di and tetrasaccharides. In MML HS 8% trisulfated saccharides present on the non-reducing end followed by 12% 2-O-N-unsubstituted saccharides, and these saccharides were resistant to heparinase III, so in BioGel P10 separation some longer chains excluded in the void volume (FIG. 2E). However, female liver HS was completely degraded into di- and tetrasaccharides. This showed the N-acetylated saccharides start with the reducing end followed by N-unsubstituted and N-sulfated saccharides and trisulfated-saccharide in the non-reducing end. The susceptible sites were highly contiguous, and the resistant fragments alternated to form tetrasaccharides (FIG. 2F).

Figure 8:
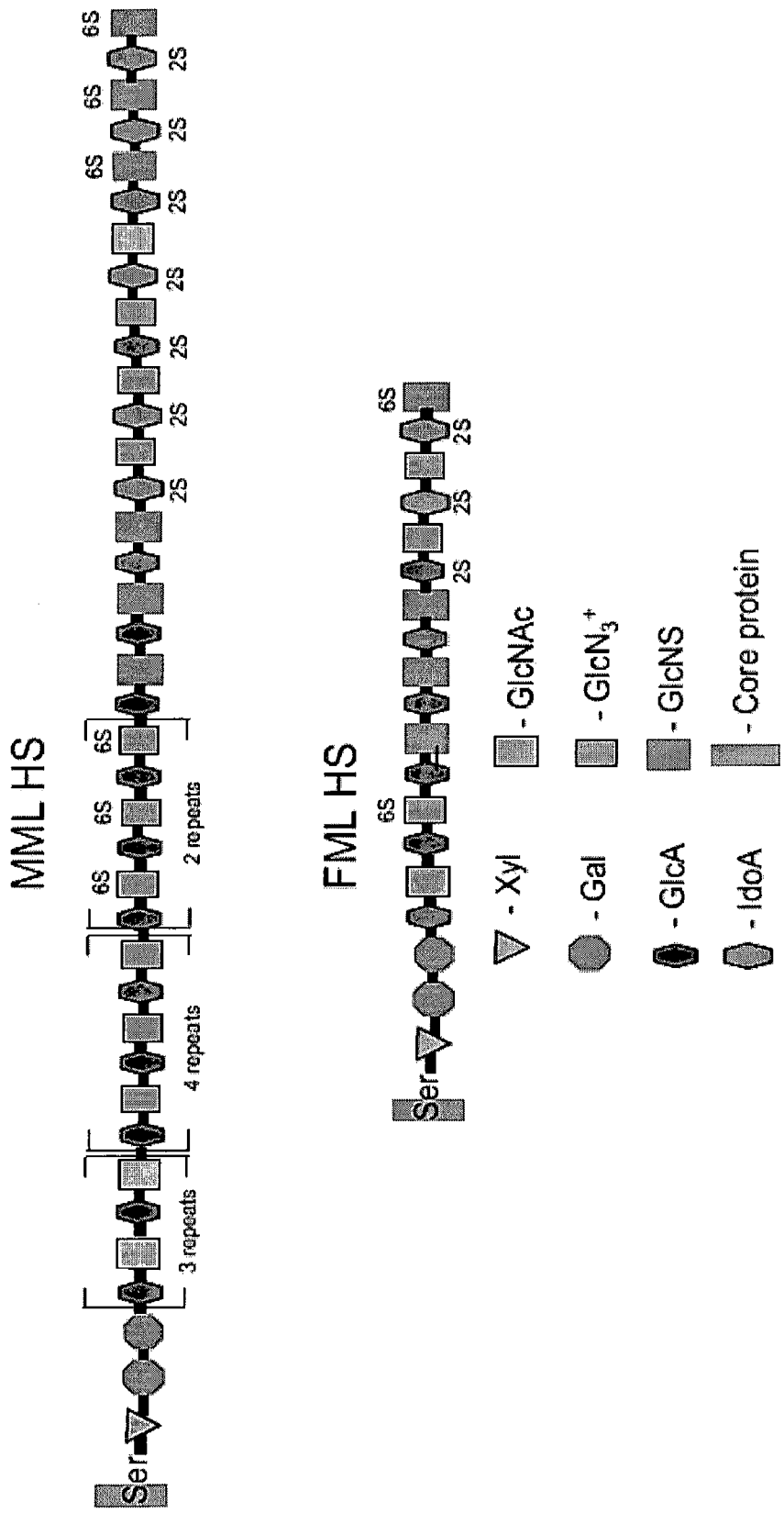
FIG. 8. Proposed structural model of male and female mouse liver intact HS chains. The structure of male and female mouse liver HS chains has been predicted with combined data obtained from chain length (FIG. 1), heparin lyase digestion patterns (FIG. 2), SAX-HPLC disaccharide profile (FIG. 3), percentage disaccharide composition (Table 1), and percentage of sulfated and N-unsubstituted disaccharides (FIG. 4). Note: 3 repeats of duplicated GlcAGlcNAc, 4 repeats of triplicated GlcA-GlcNH$_3^+$ and 2 repeats of triplicated GlcA-GlcNH$_3^+$(6S).

The structure of male and female mouse liver intact HS chains has been predicted with combined data obtained from chain length, heparinase I, II and III digestion, and % composition of differentially sulphated disaccharides. The Superdex 200 sizing column profile showed that the intact MML HS and FML HS chains composed of 30-40 or 40-50 and 6-8 disaccharides repeat, respectively. MML HS chains may consist of a substantial proportion of alternating acetylated glucosamine sequence (GlcA-GlcNAc) in the reducing end (NA domain) and N-unsubstituted glucosamine are the major proportion of mixed sequences in the middle of the HS chain, which contains $\Delta HexAGlcNH_3^+$, $\Delta HexA\text{-}GlcNH_3^+(6S)$, $\Delta HexA(2S)\text{-}GlcNH_3^+$, $\Delta HexA(2S)\text{-}GlcNAc(6S)$ and a minor portion of $\Delta HexA\text{-}GlcNSO_3$ (NA/NS domain). There are also relatively a minor proportion of about 4-5 trisulfated disaccharides ($\Delta HexA(2S)\text{-}GlcNS(6S)$) sequence on the S-domain in the non-reducing end, as illustrated in FIG. 8. FML HS chain may consist of a major proportion of N-sulfated glucosamine ($\Delta HexA\text{-}GlcNSO_3$) and also a substantial proportion of N-unsubstituted glucosamine in the middle of the HS chain, which contains $\Delta HexA\text{-}GlcNH_3^+$, $\Delta HexA\text{-}GlcNH_3^+(6S)$, $HexA(2S)\text{-}GlcNH_3^+$ (NA/NS domain). There are also a minor proportion of $\Delta HexA\text{-}GlcNAc$ present on the reducing end (N-acetyl domain) and also a minor proportion of $\Delta HexA(2S)\text{-}GlcNS(6S)$ present on the non-reducing end (N-sulfated domain) as illustrated in FIG. 8.

The present study demonstrated that the HS chains purified from gender specific liver tissue are, undeniably, almost completely distinguishable at the gross and fine structural level, therefore the question arises as to how these heparan sulfates exhibit their biologically different function. We chose human mesenchymal stem cells (hMSC) for biological functional studies, because hMSC are a potential source for cell based therapeutic studies. The use of hMSC in bone tissue engineering applications offers a powerful new tool in the development of clinical strategies for the repair of various bone disorders including osteogenesis imperfecta and osteoporesis. Our lab previously showed that heparan sulfate isolated from neuroepithelial cells increases the proliferation and osteogenic differentiation of hMSC (12). The present study showed that male and female liver HS has been shown to increase proliferation and differentiation of hMSC. We demonstrated that FML HS at lower concentration increased highest cell number in maintenance medium and MML HS at lower concentration increased highest cell number in osteogenic medium. The degree of sulfation was an important determinant of heparan sulfate ability to effect the proliferation and mineralization of hMSC. We hypothesized that FML HS with high N-sulfation was important for hMSC proliferation in normal maintenance medium, MML HS with high N-unsubstituted $GlcNH_3^+$ was important for hMSC proliferation in osteogenic medium and also MML HS with high N-unsubstituted $GlcNH_3^+$ was important for hMSC osteogenic differentiation. We tested the effect of different de-O-sulfated heparin on hMSC growth in normal and osteogenic differentiation medium. Our data showed that only de-N-sulfated heparin does not increase hMSC proliferation when compared to 10% serum in normal growth medium and 2-de-O-sulfated or 6-de-O-sulfated heparin has less effect on proliferation (data not shown). However, de-N-sulfated, 2-de-O-sulfated or 6-de-O-sulfated heparin had no effect on the hMSC proliferation in osteogenic medium (data not shown). In addition to this we tested the differentiation ability of both HS on confluent cells, the HS were added to post confluence culture of hMSC, the results showed there is no difference in the Alizarin Red S and von Kossa staining after 7, 14 and 21 days culture period (data not shown). From the above result, we suggested two possibilities to explain the effect of MML HS at lower concentration inducing high osteogenic differentiation of hMSC: (1) In osteogenic medium lower concentration of MML HS treated hMSC produce higher cell number than FML HS treated cells for 5 day culture period. Because of the higher cell number in MML HS treated cells, the initiation of osteoblast phenotype starts earlier than FML HS treated cells, this is correlated with the higher mineralization in MML HS treated cells. Yang et al (42) showed that the degree of HS sulfation was an important determinant for hMSC osteogenic differentiation and mineralization. Bovine aortic smooth muscle cells (BASMC) mineralization was inhibited by highly sulfated heparin, but N-desulfated heparin or less sulfated dermatan sulfate had no inhibition. Our data showed that total sulfation of MML HS (66% with only 18% N-sulfation) was lesser than the FML HS (85% with 62% N-sulfation), the less N-sulfated MML HS at lower concentration 300 ng/ml showed higher osteogenic differentiation and mineralization. These findings indicated that, overall, charge is the significant determinant for hMSC osteogenic differentiation and mineralization.

In control experiments, the effect of different de-O-sulfated heparins on hMSC growth in normal and osteogenic differentiation medium was also assessed. Only de-N-sulfated heparin failed to improve hMSC proliferation; 2-de-O-sulfated or 6-de-O-sulfated heparin had less effect on proliferation and neither de-N-sulfated, 2-de-O-sulfated nor 6-de-O-sulfated heparin had any effect on the hMSC proliferation in osteogenic medium (data not shown). Lower concentrations of MML HS are presumably able to induce greater levels of osteogenic differentiation in hMSCs because cell proliferation was greater over the 5 days, so resulting in faster rates of confluence, which in turn triggered more efficient osteoblast phenotypic development through better matrix mineralization; Yang et al. (46) have also shown that the degree of HS sulfation is an important determinant of rates hMSC osteogenic differentiation and mineralization. Bovine aortic smooth muscle cell mineralization is inhibited by highly sulphated heparin, but N-desulfated heparin or the less sulfated dermatan sulfate has no inhibitory activity. Our data however shows that MML HS, with its lesser sulfation levels (65% with only 11% N-sulfation) was better at triggering osteogenic differentiation and mineralization than the FML HS (85% with 61% Nsulfation). These findings indicate that HS structure, and not charge density, is the significant determinant for osteogenic differentiation and mineralization.

We showed that gender specific liver HS modulate hMSC proliferation and differentiation. Osteogenic differentiation has been genetically confirmed by sequential mRNA expression pattern of osteoblast associated marker genes and their apparition during the differentiation of hMSC. Our real-time PCR data demonstrated that HS treatment increases osteogenic differentiation related genes ALP, BSP2, OPN and Runx2. The role of these genes on osteogenic differentiation of MSC has been well defined (43-45). ALP is known to be an early marker for osteoprogenitor cells; its maximum expression was observed on day 7 of the differention period and decreased after day 7 until day 21 during the mineralization phase. Bone sialoprotein (BSP2) was described as a late marker of developing osteoblasts appearing with matrix mineralization and was maximally expressed on day 21 for both HS treated samples. These results suggest that liver HS induces upregulation of osteogenesis related genes, which facilitate hMSC to respond to osteogenic signals and subsequently matrix mineralization. Finally, morphological and genetic analysis proved the potential usefulness of gender specific liver HS on hMSC proliferation and osteogenic differentiation.

The abbreviations used are: GAGs, glycosaminoglycans; HS, heparan sulfate; TGAGs, total glycosaminoglycans; MML HS, male mouse liver hepran sulfate; FML HS, female mouse liver heparan sulfate; hMSC, human mesenchymal stem cells; ALP, alkaline phosphatase; BSP2, bone sioloprotein 2; OPN, osteopontin, dp, degree of polymerization.

REFERENCES

1. Casu, B., and Lindahl, U. (2001) *Adv Carbohyd Chem Biochem* 57, 159-206
2. Esko, J. D., and Lindahl, U. (2001) *J Clin Invest* 108, 169-173
3. Esko, J. D., and Selleck, S. B. (2002) *Annu Rev Biochem* 71, 435-471
4. Lindahl, U., Kusche-Gullberg, M., and Kjellen, L. (1998) *J Biol Chem* 273, 24979-24982
5. Walker, A., Turnbull, J. E., and Gallagher, J. T. (1994) *J Biol Chem* 269, 931-935
6. Lyon, M:, Rushton, G., Askari, J. A., Humphries, M. J., and Gallagher, J. T. (2000) *J Biol Chem* 275, 4599-4606
7. Ostrovsky, O., Berman, B., Gallagher, J., Mulloy, B., Fernig, D. G., Delehedde, M., and Ron, D. (2002) *J Biol Chem* 277, 2444-2453
8. Pye, D. A., and Gallagher, J. T. (1999) *J Biol Chem* 274, 13456-13461
9. Brickman, Y. G., Ford, M. D., Gallagher, J. T., Nurcombe, V., Bartlett, P. F., and Turnbull, J. E. (1998) *J Biol Chem* 273, 4350-4359 11
10. Nurcombe, V., Ford, M. D., Wildschut, J. A., and Bartlett, P. F. (1993) *Science* 260, 103-106
11. Jackson, R. A., Murali, S., van Wijnen, A. J., Stein, G. S., Nurcombe, V., and Cool, S. M.(2007) *J Cell Physiol* 210, 38-50
12. Christian Dombrowski, S. J. S., Peiying Chuan, Xinhong Lim, Evelyn Susanto, Amber A. Sawyer, Maria A. Wooruff, Dietmar W. Hutmacher, Victor Nurcombe, and Simon M. Cool. (2009) *Stem Cells and Development* 18, 10
13. Mauney, J. R., Volloch, V., and Kaplan, D. L. (2005) *Tissue Eng* 11, 787-802
14. Bruder, S. P., Jaiswal, N., and Haynesworth, S. E. (1997) *J Cell Biochem* 64, 278-294
15. Haynesworth, S. E., Goshima, J., Goldberg, V. M., and Caplan, A. I. (1992) *Bone* 13, 81-88
16. Pittenger, M. F., and Martin, B. J. (2004) *Circ Res* 95, 9-20
17. Hofstetter, C. P., Schwarz, E. J., Hess, D., Widenfalk, J., El Manira, A., Prockop, D. J.,and Olson, L. (2002) *Proc Natl Acad Sci USA* 99, 2199-2204
18. Sanchez-Ramos, J., Song, S., Cardozo-Pelaez, F., Hazzi, C., Stedeford, T., Willing, A., Freeman, T. B., Saporta, S., Janssen, W., Patel, N., Cooper, D. R., and Sanberg, P. R.(2000) *Exp Neurol* 164, 247-256
19. Warda, M., Toida, T., Zhang, F., Sun, P., Munoz, E., Xie, J., and Linhardt, R. J. (2006) *Glycoconj J* 23, 555-563
20. Berry, D., Shriver, Z., Venkataraman, G., and Sasisekharan, R. (2004) *Biochem Biophys Res Commun* 314, 994-1000
21. Shi, X., and Zaia, J. (2009) *J Biol Chem* 284, 11806-11814
22. Toida, T., Yoshida, H., Toyoda, H., Koshiishi, I., Imanari, T., Hileman, R. E., Fromm, J. R., and Linhardt, R. J. (1997) *Biochem J* 322 (Pt 2), 499-506
23. Gandhi, N. S., and Mancera, R. L. (2008) *Chem Biol Drug Des* 72, 455-482
24. Robinson, C. J., Harmer, N. J., Goodger, S. J., Blundell, T. L., and Gallagher, J. (2005) *J Biol Chem* 280, 42274-42282
25. Linhardt, R. J., Rice, K. G., Kim, Y. S., Lohse, D. L., Wang, H. M., and Loganathan, D. (1988) *Biochem J* 254, 781-787
26. Hovingh, P., and Linker, A. (1970) *J Biol Chem* 245, 6170-6175
27. Linhardt, R. J., Turnbull, J. E., Wang, H. M., Loganathan, D., and Gallagher, J. T. (1990) *Biochemistry* 29, 2611-2617
28. Linker, A., and Sampson, P. (1960) *Biochim Biophys Acta* 43, 366-368
29. Lohse, D. L., and Linhardt, R. J. (1992) *J Biol Chem* 267, 24347-24355
30. Perlin, A. S., Mackie, D. M., and Dietrich, C. P. (1971) *Carbohydr Res* 18, 185-194
31. Turnbull, J. E., and Gallagher, J. T. (1990) *Biochem J* 265, 715-724
32. Turnbull, J. E., and Gallagher, J. T. (1991) *Biochem J* 273 (Pt 3), 553-559
33. Turnbull, J. E., and Gallagher, J. T. (1991) *Biochem J* 277 (Pt 2), 297-303
34. Desai, U. R., Wang, H. M., and Linhardt, R. J. (1993) *Biochemistry* 32, 8140-8145
35. Nader, H. B., Porcionatto, M. A., Tersariol, I. L., Pinhal, M. A., Oliveira, F. W., Moraes, C. T., and Dietrich, C. P. (1990) *J Biol Chem* 265, 16807-16813
36. Wei, Z., Lyon, M., and Gallagher, J. T. (2005) *J Biol Chem* 280, 15742-15748
37. Lindblom, A., and Fransson, L. A. (1990) *Glycoconj J* 7, 545-562
38. Moffat, C. F., McLean, M: W., Long, W. F., and Williamson, F. B. (1991) *EurJ Biochem* 202, 531-541
39. Rhomberg, A. J., Shriver, Z., Biemann, K., and Sasisekharan, R. (1998) *Proc Natl Acad Sci USA* 95, 12232-12237
40. Moffat, C. F., McLean, M. W., Long, W. F., and Williamson, F. B. (1991) *EurJ Biochem* 197, 449-459
41. Wu, Z. L., and Lech, M. (2005) *J Biol Chem* 280, 33749-33755 12
42. Yang, L., Butcher, M., Simon, R. R., Osip, S. L., and Shaughnessy, S. G. (2005) *Atherosclerosis* 179, 79-86
43. Diefenderfer, D. L., Osyczka, A. M., Garino, J. P., and Leboy, P. S. (2003) *J Bone Joint Surg Am* 85-A Suppl 3, 19-28
44. Dragoo, J. L., Choi, J. Y., Lieberman, J. R., Huang, J., Zuk, P. A., Zhang, J., Hedrick, M. H., and Benhaim, P. (2003) *J Orthop Res* 21, 622-629
45. Shui, C., Spelsberg, T. C., Riggs, B. L., and Khosla, S. (2003) *J Bone Miner Res* 18, 213-221

The invention claimed is:

1. A method of treating a bone fracture in a patient, the method comprising administration of a therapeutically effective amount of male mouse liver heparan sulphate (MML HS) to the patient wherein the MML HS has N-sulfation of between about 14% and about 22%.

2. The method of claim 1 wherein the method comprises administering MML HS to the tissue surrounding the fracture.

3. The method of claim 1 wherein administration of MML HS comprises injection of MML HS to the tissue surrounding the fracture.

4. The method of claim 1 wherein the method further comprises administering mesenchymal stem cells to the patient.

5. A method of treating a bone fracture in a patient, the method comprising surgically implanting a biocompatible implant or prosthesis, which implant or prosthesis comprises a biomaterial and MML HS, into tissue of the patient at or surrounding the site of fracture, wherein the MML HS has N-sulfation of between about 14% and about 22%.

6. A method for the repair, replacement or regeneration of bone tissue in a human or animal patient in need of such treatment, the method comprising:
 (i) culturing mesenchymal stem cells in vitro in contact with MML HS for a period of time sufficient for said cells to form bone tissue or bone precursor cells, wherein the MML HS has N-sulfation of between about 14% and about 22%;
 (ii) collecting said bone tissue or bone precursor cells; and
 (iii) implanting said bone tissue or bone precursor cells into the body of the patient at a site of injury or disease to repair, replace or regenerate bone tissue in the patient.

7. A method according to claim 1 wherein the MML HS has:
 (i) total sulfation of between about 60% and about 70%; and/or
 (ii) total O-sulfation of between about 44% and about 52%; and/or
 (iii) N-sulfation of between about 14% and about 22%; and/or
 (iv) 6-O-sulfation of between about 22% and about 30%; and/or
 (v) 2-O-sulfation of between about 18% and about 26%.

8. A method according to claim 1 wherein the MML HS has:
 (i) total sulfation of about 65% or about 66%; and/or
 (ii) total O-sulfation of about 47%, about 48% or about 49%; and/or
 (iii) N-sulfation of about 17%, about 18% or about 19%; and/or
 (iv) 6-O-sulfation of about 25%, about 26% or about 27%; and/or
 (v) 2-O-sulfation of about 21%, about 22% or about 23%.

9. A method according to claim 1 wherein the MML HS has an N-unsubstituted disaccharide content of between about 53% and about 61%.

10. A method according to claim 1 wherein the MML HS has an N-unsubstituted disaccharide content of about 56%, about 57% or about 58%.

11. A method according to claim 1 wherein the MML HS has a disaccharide composition within ±10% of the values shown for each disaccharide in the Male Liver HS column in Table 2.

12. A method according to claim 1 wherein the MML HS has a disaccharide composition within ±5% of the values shown for each disaccharide in the Male Liver HS column in Table 2.

13. A method according to claim 1 wherein the MML HS is obtained by a method comprising conducting size exclusion chromatography on a male mouse liver heparan sulphate preparation to identify heparan sulphate fractions of different molecular weight followed by selection of the major high molecular weight fraction.

14. A method according to claim 5 wherein the MML HS has:
   (i) total sulfation of between about 60% and about 70%; and/or
   (ii) total O-sulfation of between about 44% and about 52%; and/or
   (iii) N-sulfation of between about 14% and about 22%; and/or
   (iv) 6-O-sulfation of between about 22% and about 30%; and/or
   (v) 2-O-sulfation of between about 18% and about 26%.

15. A method according to claim 5 wherein the MML HS has:
   (i) total sulfation of about 65% or about 66%; and/or
   (ii) total O-sulfation of about 47%, about 48% or about 49%; and/or
   (iii) N-sulfation of about 17%, about 18% or about 19%; and/or
   (iv) 6-O-sulfation of about 25%, about 26% or about 27%; and/or
   (v) 2-O-sulfation of about 21%, about 22% or about 23%.

16. A method according to claim 5 wherein the MML HS has an N-unsubstituted disaccharide content of between about 53% and about 61%.

17. A method according to claim 5 wherein the MML HS has an N-unsubstituted disaccharide content of about 56%, about 57% or about 58%.

18. A method according to claim 5 wherein the MML HS has a disaccharide composition within ±10% of the values shown for each disaccharide in the Male Liver HS column in Table 2.

19. A method according to claim 5 wherein the MML HS has a disaccharide composition within ±5% of the values shown for each disaccharide in the Male Liver HS column in Table 2.

20. A method according to claim 5 wherein the MML HS is obtained by a method comprising conducting size exclusion chromatography on a male mouse liver heparan sulphate preparation to identify heparan sulphate fractions of different molecular weight followed by selection of the major high molecular weight fraction.

* * * * *

SEQUENCE LISTING

<160> NUMBER OF SEQ ID NOS: 15

<210> SEQ ID NO 1
<211> LENGTH: 20
<212> TYPE: DNA
<213> ORGANISM: Artificial sequence
<220> FEATURE:
<223> OTHER INFORMATION: Synthetic sequence: Forward primer

<400> SEQUENCE: 1
ttcgaggccc tgtaattgga                                                    20

<210> SEQ ID NO 2
<211> LENGTH: 26
<212> TYPE: DNA
<213> ORGANISM: Artificial sequence
<220> FEATURE:
<223> OTHER INFORMATION: Synthetic sequence: Reverse primer

<400> SEQUENCE: 2
gcagcaactt taatatacgc tattgg                                             26

<210> SEQ ID NO 3
<211> LENGTH: 18
<212> TYPE: DNA
<213> ORGANISM: Artificial sequence
<220> FEATURE:
<223> OTHER INFORMATION: Synthetic sequence: Probe

<400> SEQUENCE: 3
agtccacttt aaatcctt                                                      18

<210> SEQ ID NO 4
<211> LENGTH: 20
<212> TYPE: DNA
<213> ORGANISM: Artificial sequence
<220> FEATURE:
<223> OTHER INFORMATION: Synthetic sequence: Forward primer

<400> SEQUENCE: 4
atgccctgga gcttcagaag                                                    20

<210> SEQ ID NO 5
<211> LENGTH: 20
<212> TYPE: DNA
<213> ORGANISM: Artificial sequence
<220> FEATURE:
<223> OTHER INFORMATION: Synthetic sequence: Reverse primer

<400> SEQUENCE: 5
tggtggagct gacccttgag                                                    20

<210> SEQ ID NO 6
<211> LENGTH: 20
<212> TYPE: DNA
<213> ORGANISM: Artificial sequence
<220> FEATURE:
<223> OTHER INFORMATION: Synthetic sequence: Probe
<220> FEATURE:
<221> NAME/KEY: misc_feature
<222> LOCATION: (5)..(7)
<223> OTHER INFORMATION: LNA base

<400> SEQUENCE: 6
acgtggctaa gaatgtcatc                                                    20

-continued

```
<210> SEQ ID NO 7
<211> LENGTH: 23
<212> TYPE: DNA
<213> ORGANISM: Artificial sequence
<220> FEATURE:
<223> OTHER INFORMATION: Synthetic sequence: Forward primer

<400> SEQUENCE: 7
agaggaagca atcaccaaaa tga                                          23

<210> SEQ ID NO 8
<211> LENGTH: 21
<212> TYPE: DNA
<213> ORGANISM: Artificial sequence
<220> FEATURE:
<223> OTHER INFORMATION: Synthetic sequence: Reverse primer

<400> SEQUENCE: 8
ttgagaaagc acaggccatt c                                            21

<210> SEQ ID NO 9
<211> LENGTH: 20
<212> TYPE: DNA
<213> ORGANISM: Artificial sequence
<220> FEATURE:
<223> OTHER INFORMATION: Synthetic sequence: Probe
<220> FEATURE:
<221> NAME/KEY: misc_feature
<222> LOCATION: (4)..(6)
<223> OTHER INFORMATION: LNA base

<400> SEQUENCE: 9
ctgctttaat tttgctcagc                                              20

<210> SEQ ID NO 10
<211> LENGTH: 23
<212> TYPE: DNA
<213> ORGANISM: Artificial sequence
<220> FEATURE:
<223> OTHER INFORMATION: Synthetic sequence: Forward primer

<400> SEQUENCE: 10
acatcacctc acacatggaa agc                                          23

<210> SEQ ID NO 11
<211> LENGTH: 24
<212> TYPE: DNA
<213> ORGANISM: Artificial sequence
<220> FEATURE:
<223> OTHER INFORMATION: Synthetic sequence: Reverse primer

<400> SEQUENCE: 11
gctgactcgt ttcataactg tcct                                         24

<210> SEQ ID NO 12
<211> LENGTH: 20
<212> TYPE: DNA
<213> ORGANISM: Artificial sequence
<220> FEATURE:
<223> OTHER INFORMATION: Synthetic sequence: Probe
<220> FEATURE:
<221> NAME/KEY: misc_feature
<222> LOCATION: (5)..(7)
<223> OTHER INFORMATION: LNA base

<400> SEQUENCE: 12
cttctgattg ggacagccgt                                              20
```

-continued

```
<210> SEQ ID NO 13
<211> LENGTH: 21
<212> TYPE: DNA
<213> ORGANISM: Artificial sequence
<220> FEATURE:
<223> OTHER INFORMATION: Synthetic sequence: Forward primer

<400> SEQUENCE: 13
aggcatgtcc ctcggtatgt c                                              21

<210> SEQ ID NO 14
<211> LENGTH: 21
<212> TYPE: DNA
<213> ORGANISM: Artificial sequence
<220> FEATURE:
<223> OTHER INFORMATION: Synthetic sequence: Reverse primer

<400> SEQUENCE: 14
gaagggtcca ctctggcttt g                                              21

<210> SEQ ID NO 15
<211> LENGTH: 20
<212> TYPE: DNA
<213> ORGANISM: Artificial sequence
<220> FEATURE:
<223> OTHER INFORMATION: Synthetic sequence: Probe
<220> FEATURE:
<221> NAME/KEY: misc_feature
<222> LOCATION: (5)..(8)
<223> OTHER INFORMATION: LNA base

<400> SEQUENCE: 15
acacctacct gccaccaccc                                                20
```